US012665052B2

(12) United States Patent
Eidsaa et al.

(10) Patent No.: US 12,665,052 B2
(45) Date of Patent: Jun. 23, 2026

(54) METHOD AND SYSTEM FOR BINDING AFFINITY PREDICTION AND METHOD OF GENERATING A CANDIDATE PROTEIN-BINDING PEPTIDE

(71) Applicant: NEC ONCOIMMUNITY AS, Oslo (NO)

(72) Inventors: Marius Eidsaa, Oslo (NO); Richard Stratford, Oslo (NO); Trevor Clancy, Oslo (NO)

(73) Assignee: NEC ONCOIMMUNITY AS, Oslo (NO)

( * ) Notice: Subject to any disclaimer, the term of this patent is extended or adjusted under 35 U.S.C. 154(b) by 989 days.

(21) Appl. No.: 17/282,708

(22) PCT Filed: Oct. 4, 2019

(86) PCT No.: PCT/EP2019/076954
§ 371 (c)(1),
(2) Date: Apr. 2, 2021

(87) PCT Pub. No.: WO2020/070307
PCT Pub. Date: Apr. 9, 2020

(65) Prior Publication Data
US 2021/0391032 A1 Dec. 16, 2021

(30) Foreign Application Priority Data

Oct. 5, 2018 (EP) .................................... 18198984

(51) Int. Cl.
*G16B 20/30* (2019.01)
*G16B 15/30* (2019.01)
(52) U.S. Cl.
CPC ............. *G16B 20/30* (2019.02); *G16B 15/30* (2019.02)

(58) Field of Classification Search
CPC ................................ G16B 20/30; G16B 15/30
See application file for complete search history.

(56) References Cited

U.S. PATENT DOCUMENTS

2013/0330335 A1 12/2013 Bremel et al.

FOREIGN PATENT DOCUMENTS

JP        2008-222574 A      9/2008
WO    WO 2004/003221      1/2004

OTHER PUBLICATIONS

Karosiene, E., Rasmussen, M., Blicher, T., Lund, O., Buus, S., & Nielsen, M. (2013). NetMHCIIpan-3. 0, a common pan-specific MHC class II prediction method including all three human MHC class II isotypes, HLA-DR, HLA-DP and HLA-DQ. Immunogenetics, 65, 711-724. (Year: 2013) (Year: 2013).*

(Continued)

*Primary Examiner* — Kaitlyn L Minchella
*Assistant Examiner* — Noah A. Auger
(74) *Attorney, Agent, or Firm* — Foley & Lardner LLP

(57) ABSTRACT

In a first aspect of the present disclosure, there is provided a computer-implemented method of predicting a binding affinity of a query binder molecule to a query target molecule, the query binder molecule having a first amino acid sequence and the query target molecule having a second amino acid sequence, the method comprising: computing, with the at least one processor, the binding affinity for the query binder molecule to the query target molecule as a weighted combination of reference binding values of reference binder-target subsequence pairs, wherein weights of the weighted combination are based on similarity scores.

14 Claims, 13 Drawing Sheets

(56) References Cited

OTHER PUBLICATIONS

Bininda-Emonds, O. R. (2005). transAlign: using amino acids to facilitate the multiple alignment of protein-coding DNA sequences. BMC bioinformatics, 6, 1-6. (Year: 2005) (Year: 2005).*

Tanabe, S. (2007). Epitope peptides and immunotherapy. Current Protein and Peptide Science, 8(1), 109-118. (Year: 2007) (Year: 2007).*

Goodswen, S. J., Kennedy, P. J., & Ellis, J. T. (2014). Enhancing in silico protein-based vaccine discovery for eukaryotic pathogens using predicted peptide-MHC binding and peptide conservation scores. PloS one, 9(12), e115745. (Year: 2014).*

Aldous, A. R., & Dong, J. Z. (2018). Personalized neoantigen vaccines: A new approach to cancer immunotherapy. Bioorganic & medicinal chemistry, 26(10), 2842-2849. (Year: 2018).*

Giguere, S., Laviolette, F., Marchand, M., Tremblay, D., Moineau, S., Liang, X., ... & Corbeil, J. (2015). Machine learning assisted design of highly active peptides for drug discovery. PLoS computational biology, 11(4), e1004074. (Year: 2015).*

Giguère, S., Drouin, A., Lacoste, A., Marchand, M., Corbeil, J., & Laviolette, F. (2013). MHC-NP: predicting peptides naturally processed by the MHC. Journal of immunological methods, 400, 30-36. (Year: 2013).*

Antes, I., Siu, S. W., & Lengauer, T. (2006). DynaPred: a structure and sequence based method for the prediction of MHC class I binding peptide sequences and conformations. Bioinformatics, 22(14), e16-e24. (Year: 2006).*

Morten Nielsen et al: "NetMHCpan-3.0; improved prediction of binding to MHC class I molecules integrating information from multiple receptor and peptide length datasets", Genome Medicine, vol. 8, No. 1, Mar. 30, 2015, XP055571478.

Patent Cooperation Treaty, International Search Report, PCT/EP2019/076954, dated Dec. 20, 2019, in 2 pages.

European Patent Office, Extended European Search Report, 18198984.9, dated Mar. 28, 2019 in 11 pages.

* cited by examiner

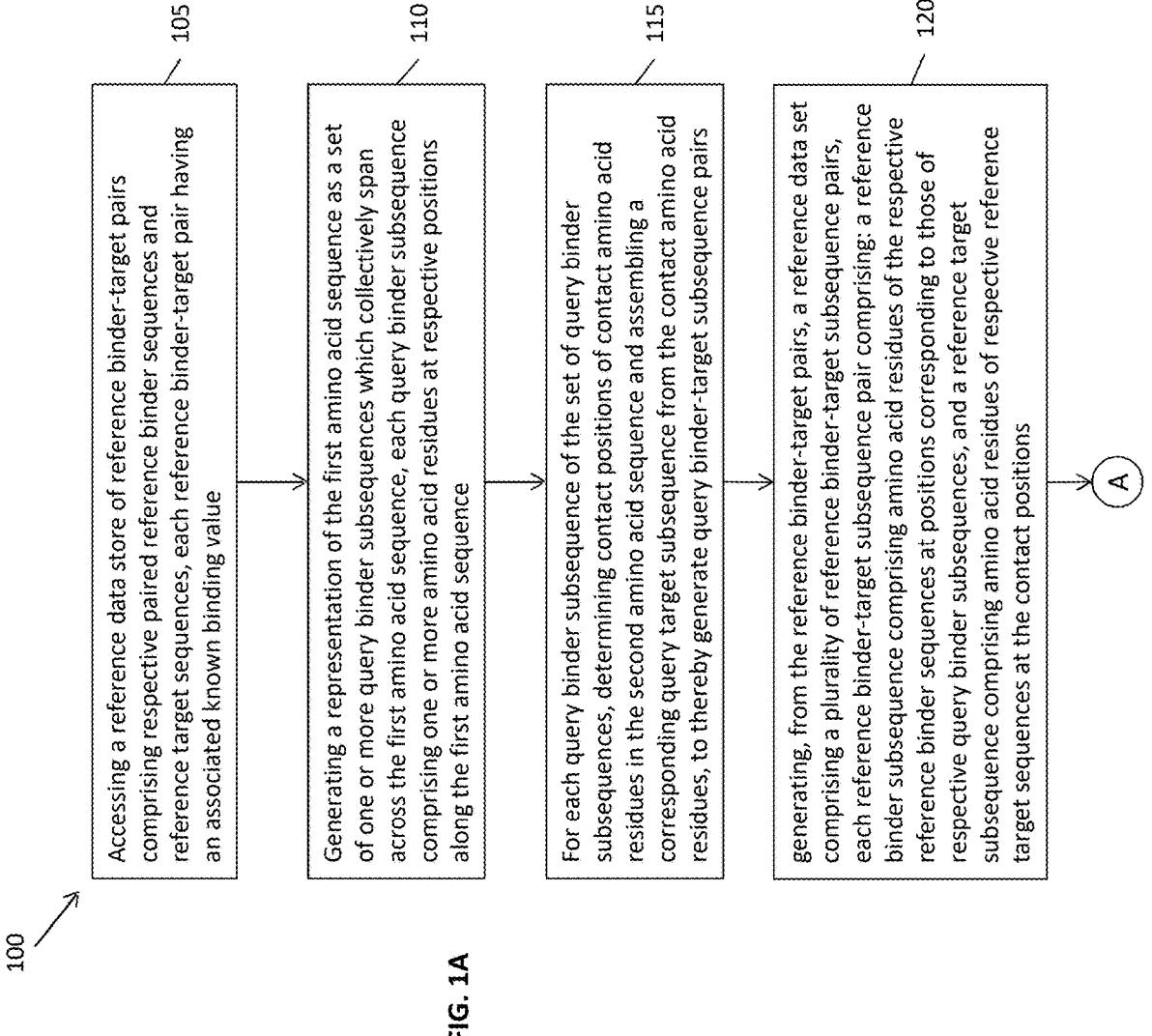

100

Accessing a reference data store of reference binder-target pairs comprising respective paired reference binder sequences and reference target sequences, each reference binder-target pair having an associated known binding value

105

Generating a representation of the first amino acid sequence as a set of one or more query binder subsequences which collectively span across the first amino acid sequence, each query binder subsequence comprising one or more amino acid residues at respective positions along the first amino acid sequence

110

For each query binder subsequence of the set of query binder subsequences, determining contact positions of contact amino acid residues in the second amino acid sequence and assembling a corresponding query target subsequence from the contact amino acid residues, to thereby generate query binder-target subsequence pairs

115 generating, from the reference binder-target pairs, a reference data set comprising a plurality of reference binder-target subsequence pairs, each reference binder-target subsequence pair comprising: a reference binder subsequence comprising amino acid residues of the respective reference binder sequences at positions corresponding to those of respective query binder subsequences, and a reference target subsequence comprising amino acid residues of respective reference target sequences at the contact positions

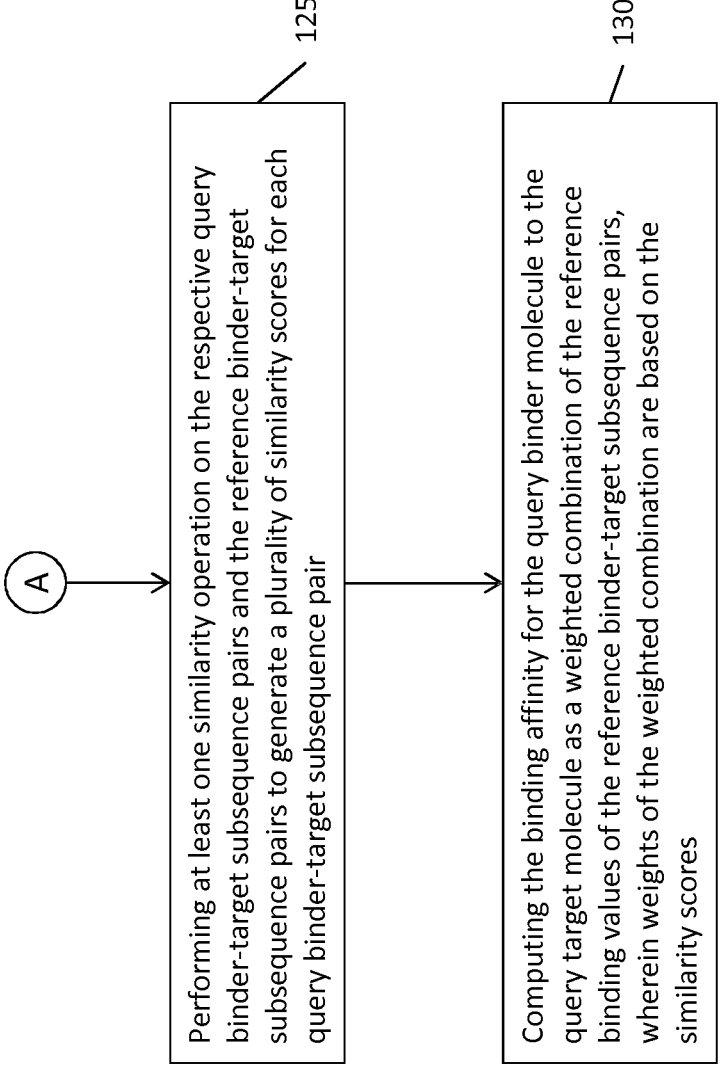

(A)

125

Performing at least one similarity operation on the respective query binder-target subsequence pairs and the reference binder-target subsequence pairs to generate a plurality of similarity scores for each query binder-target subsequence pair

130

Computing the binding affinity for the query binder molecule to the query target molecule as a weighted combination of the reference binding values of the reference binder-target subsequence pairs, wherein weights of the weighted combination are based on the similarity scores

Element-wise substitution matrix (dummy values)

| Amino acid in sequence 1 | Amino acid in sequence 2 | Substitution value |
|---|---|---|
| A | A | 3 |
| B | B | 4 |
| C | C | 5 |
| D | D | 3 |
| E | E | 4 |
| F | F | 5 |
| X | X | 3 |
| Y | Y | 4 |
| A | X | 1 |
| B | Y | -1 |
| F | X | 0 |

MHC HOPs at position 1

| | |
|---|---|
| HLA-X | ABC |
| HLA-Y | ABC |
| HLA-Z | ABC |

MHC HOPs at position 2

| | |
|---|---|
| HLA-X | DEF |
| HLA-Y | DEF |
| HLA-Z | DEX |

MHC HOPs at position 3

| | |
|---|---|
| HLA-X | ABD |
| HLA-Y | XYD |
| HLA-Z | XYD |

Power values

| | |
|---|---|
| MHC SeqSim 2-mers | 2 |
| MHC NbrSim 2-mers | 5 |

Anchor weights

| | |
|---|---|
| Pos 1 | 2 |
| Pos 2 | 7 |
| Pos 3 | 3 |
| Pos (1, 2) | 9 |
| Pos (1, 3) | 5 |

FIG. 4

Reference data

| Allele | Peptide | Binding affinity | MHC HOP (1,2) | Peptide HOP (1,2) | MHC HOP (1,3) | Peptide HOP (1,3) |
|---|---|---|---|---|---|---|
| HLA-X | ABCDEFGHI | 0.9 | ABCDEF | AB | ABCABD | AC |
| HLA-X | XBCDEFGHI | 0.2 | ABCDEF | XB | ABCABD | XC |
| HLA-X | AXCDEFGHI | 0.6 | ABCDEF | AX | ABCABD | AC |
| HLA-X | ABXDEFGHI | 0.8 | ABCDEF | AB | ABCABD | AX |
| HLA-X | YBCDEFGHI | 0.1 | ABCDEF | YB | ABCABD | YC |
| HLA-Y | ABCDEFGHI | 0.8 | ABCDEF | AB | ABCXYD | AC |
| HLA-Y | XBCDEFGHI | 0.1 | ABCDEF | XB | ABCXYD | XC |
| HLA-Y | AXCDEFGHI | 0.3 | ABCDEF | AX | ABCXYD | AC |
| HLA-Y | ABXDEFGHI | 0.9 | ABCDEF | AB | ABCXYD | AX |
| HLA-Y | YBCDEFGHI | 0.3 | ABCDEF | YB | ABCXYD | YC |
| HLA-Y | ABYDEFGHI | 0.5 | ABCDEF | AB | ABCXYD | AY |

Unique HOP averages (1,2)

| MHC HOP | Peptide HOP | Binding affinity |
|---|---|---|
| ABCDEF | AB | 0.78 |
| ABCDEF | XB | 0.15 |
| ABCDEF | AX | 0.45 |
| ABCDEF | YB | 0.2 |

510

Unique HOP averages (1,3)

| MHC HOP | Peptide HOP | Binding affinity |
|---|---|---|
| ABCABD | AC | 0.75 |
| ABCABD | XC | 0.2 |
| ABCABD | AX | 0.8 |
| ABCABD | YC | 0.1 |
| ABCXYD | AC | 0.55 |
| ABCXYD | XC | 0.1 |
| ABCXYD | AX | 0.9 |
| ABCXYD | YC | 0.3 |
| ABCXYD | AY | 0.5 |

Reference data decomposed to HOPs for position (1, 2)

| MHC HOP | Peptide HOP | Binding affinity |
|---------|-------------|------------------|
| ABCDEF | AB | 0.9 |
| ABCDEF | XB | 0.2 |
| ABCDEF | AX | 0.6 |
| ABCDEF | AB | 0.8 |
| ABCDEF | YB | 0.1 |
| ABCDEF | AB | 0.8 |
| ABCDEF | XB | 0.1 |
| ABCDEF | AX | 0.3 |
| ABCDEF | AB | 0.9 |
| ABCDEF | YB | 0.3 |
| ABCDEF | AB | 0.5 |

Unique HOP averages

| MHC HOP | Peptide HOP | Binding affinity |
|---------|-------------|------------------|
| ABCDEF | AB | 0.78 |
| ABCDEF | XB | 0.15 |
| ABCDEF | AX | 0.45 |
| ABCDEF | YB | 0.2 |

FIG. 6

Reference data decomposed to HOPs for position (1, 3)

| MHC HOP | Peptide HOP | Binding affinity |
|---------|-------------|------------------|
| ABCABD  | AC          | 0.9              |
| ABCABD  | XC          | 0.2              |
| ABCABD  | AC          | 0.6              |
| ABCABD  | AX          | 0.8              |
| ABCABD  | YC          | 0.1              |
| ABCXYD  | AC          | 0.8              |
| ABCXYD  | XC          | 0.1              |
| ABCXYD  | AC          | 0.3              |
| ABCXYD  | AX          | 0.9              |
| ABCXYD  | YC          | 0.3              |
| ABCXYD  | AY          | 0.5              |

FIG. 7

METHOD AND SYSTEM FOR BINDING AFFINITY PREDICTION AND METHOD OF GENERATING A CANDIDATE PROTEIN-BINDING PEPTIDE

BACKGROUND

The present disclosure relates to computational predictions of binding affinity between binder molecules and target molecules, for example, between peptides and proteins, or between pairs of proteins.

An understanding of molecular binding is important in many biological contexts. For example, in the development of drug or biologic therapies it is important to understand how, and how strongly, a candidate therapeutic molecule binds to its intended target, or a pathogenic peptide binds to a cell-surface protein.

In vertebrates, the major histocompatibility complex (MHC) molecules have evolved to bind pathogenic or self peptides, forming an MHC-peptide complex that is subsequently transported to the cell surface by the cellular machinery. The MHC molecules are typically designated MHC class I or MHC class II. Although similar in function, MHC class I molecules deliver peptides derived endogenously from within a cell to the cell surface, whereas MHC class II molecules are responsible for delivery of exogenous, or extracellular, peptides to the cell surface, where subsequent recognition of the peptides by CD8+ (cytotoxic) or CD4+ (helper) T cells occurs. This recognition then initiates or propagates an immune response. There are several critical interdependent steps in the class I antigen presentation pathway, including antigen processing by the proteasome and TAP transport, and the class II pathway including internalisation of exogenous antigen, capture in endosomes and subsequent protease mediated hydrolysis. However, the MHC-binding step is the most important selection mechanism for both the endogenous and exogenous antigen processing pathways and is requisite (although not sufficient) for the successful presentation of pathogenic peptides, and for mutated neoantigens in cancer. The importance of MHC binding as a central tenet of the adaptive immune response has led to extensive research in the accurate identification and measurement of MHC-peptide binding affinity within several research fields, including infectious disease, vaccine development, transplantation, autoimmune disease, and cancer immunotherapy.

In humans, MHC class I molecules are coded by three polymorphic genes in the class I human leukocyte antigen (HLA) genomic region termed HLA-A, HLA-B and HLA-C. All three genes are extremely polymorphic, with more than 10,000 characterised alleles. Similar to class I, MHC class II molecules are encoded by three polymorphic genes termed HLA-DR, HLA-DQ and HLA-DP. The high degree of polymorphism in the MHC molecules, and the inherent variability of amino acids in antigenic peptide sequences, has driven the need for the development of computational tools capable of accurately predicting MHC-peptide binding affinities, resulting in numerous successful approaches. However, availability of large amounts of experimental data is required to train good predictive models. For several years, great experimental efforts have been made to accumulate MHC-peptide binding affinity measurements for some of the most common MHC alleles. Nonetheless, the clear majority of alleles are still not adequately covered in presently available databases of MHC-peptide binding affinity measurements. For several of these alleles, the best performing predictors are often "allele-specific" models, meaning they are only trained on, and can thus also only predict for, one specific MHC allele. The allele-specific models generally require a substantial amount of binding affinity data, making them suitable only for a small number of well-studied alleles. Several algorithmic approaches have leveraged the availability of sufficient training data to build successful allele-specific approaches, ranging from neural networks to support vector machines (SVMs), but also more mechanistically interpretable approaches such as position specific scoring matrices (PSSM) or molecular modelling based approaches.

Several attempts have been made to create computational tools which implement "pan-allele" models that can generate predictions of binding affinity across different MHC alleles. These have primarily been trained using neural network based approaches and generally fall into one of two categories. A "pan-specific" model is restricted to predictions among the alleles it has trained on, while a "pan" model makes predictions based on MHC sequences, and can thus make predictions for arbitrary or de novo MHC alleles.

The overarching aim of pan-allele models is to predict general binding patterns, applicable across all alleles, enabling predictions even for alleles with little or no training data. In order to do so, it has generally been thought desirable for a model to reflect the physical interactions between the MHC molecule and the peptide, for example by using crystal structure data obtained for MHC-peptide complexes.

From the structure data it is known that the peptide-interacting component of an MHC molecule consists of a highly polymorphic binding cleft, made from two amino acid chains forming two almost parallel helices. For MHC class I, it has been observed that only a small number of the 182 amino acids forming the MHC class I molecules are in the immediate vicinity of a bound peptide amino acid (for example, within a distance of 4.0 Angstroms of any amino acid of a bound peptide). These peptide-proximal MHC amino acids outlining the binding cleft can be referred to as the "pseudo-sequence" (see, for example, Nielsen et al, *PLoS One* 2007, 2: e796, the contents of which are incorporated herein by reference in their entirety).

The way in which the peptide is bound to the MHC protein can be summarised using what has been referred to in the literature as a "contact point map", "contact position map", or simply "contact map" (each of which will be used interchangeably below). In general, a contact point map defines a mapping between amino acid residues of a binder molecule (such as a peptide) and corresponding amino acid residues of a target molecule (such as an MHC protein) to which it is bound, where the corresponding amino acid residues are residues of the target molecule which are within a threshold distance from the amino acid residues in the binder molecule such that they have sufficient physical interaction with the binder molecule residues to contribute to formation of the binder-target complex. For example, residues which are within 4 Angstrom of the binder molecule residues may form part of the contact point map.

A contact point map may be represented as a table or a matrix in which rows represent amino acids of the target molecule pseudo-sequence and columns represent amino acids of the binder molecule. An entry (t, b) of the table is equal to 1 if the binder molecule amino acid b is within the predefined distance of the pseudo-sequence amino acid t. A specific example of a contact point map for MHC class I molecules may be found in Nielsen et al. A further example for MHC class II molecules may be found in Karosiene et al,

*Immunogenetics* 2013, 65:711-724, the contents of which are incorporated herein by reference in their entirety.

Contact point maps have been used to build so-called "pocket"-based models of peptide-MHC binding, in which each amino acid (monomer) of the peptide is treated as a separate binding unit which is bound to one or more amino acids of the MHC pseudo-sequence assumed to be in the proximity to the monomer according to the contact point map. The proximal amino acids of the MHC pseudo-sequence may be referred to as a "binding pocket". This enables prediction of MHC binding patterns for alleles where little or no training data is available, by matching the binding pockets to similar occurrences of structural subunits in the training data, and then adding together all the binding affinity contributions from the matching subunits.

It is desirable to provide a method of predicting binding affinities which improves on the above approaches, or at least provides a useful alternative.

SUMMARY

In general terms, the present disclosure proposes a method and system of predicting binding affinity in which the pocket approach of the prior art is extended beyond the use of monomers. Accordingly, in certain embodiments, it is possible to capture the influence of contextual amino acid n-mer length residues (where n is between 2 and the length of the peptide) in both the peptide and MHC molecule.

In a first aspect of the present disclosure, there is provided a computer-implemented method of predicting a binding affinity of a query binder molecule to a query target molecule, the query binder molecule having a first amino acid sequence and the query target molecule having a second amino acid sequence, the method comprising: accessing, with at least one processor, a reference data store of reference binder-target pairs comprising respective paired reference binder sequences and reference target sequences, each reference binder-target pair having an associated known binding value; generating, with the at least one processor, a representation of the first amino acid sequence as a set of one or more query binder subsequences which collectively span across the first amino acid sequence, each query binder subsequence comprising one or more amino acid residues at respective positions along the first amino acid sequence; for each query binder subsequence of the set of query binder subsequences, determining contact positions of contact amino acid residues in the second amino acid sequence and assembling a corresponding query target subsequence from the contact amino acid residues, to thereby generate query binder-target subsequence pairs; generating, with the at least one processor, from the reference binder-target pairs, a reference data set comprising a plurality of reference binder-target subsequence pairs, each reference binder-target subsequence pair comprising: a reference binder subsequence comprising amino acid residues of the respective reference binder sequences at positions corresponding to those of respective query binder subsequences, and a reference target subsequence comprising amino acid residues of respective reference target sequences at the contact positions; wherein each reference binder-target subsequence pair is assigned a reference binding value based on the known binding value of the reference binder-target pair from which it was generated; performing, with the at least one processor, at least one similarity operation on the respective query binder-target subsequence pairs and the reference binder-target subsequence pairs to generate a plurality of similarity scores for each query binder-target subsequence pair; and computing, with the at least one processor, the binding affinity for the query binder molecule to the query target molecule as a weighted combination of the reference binding values of the reference binder-target subsequence pairs, wherein weights of the weighted combination are based on the similarity scores.

Preferably at least one query binder subsequence may comprise at least two amino acid residues.

The predicted binding affinity is more reliably determined than techniques of the art by considering the context relationships of MHC-binding pockets and improves the accuracy of the binding affinity prediction in a way which better represents the biological complexity of MHC-peptide binding. The technique effectively reduces combinatorial complexity of modelling when compared to existing techniques.

The similarity operation may generate respective similarity scores by generating a first similarity score for a comparison between a query binder subsequence and reference binder subsequence, and a second similarity score for a comparison between a query target subsequence and reference target subsequence, and combines the first similarity score and second similarity score.

Preferably the first similarity score may be given a non-zero value in the case of an exact match, and a zero value otherwise.

More preferably the second similarity score may be given a non-zero value in the case of an exact match, and a zero value otherwise.

In certain embodiments the similarity operation may comprise a sequence alignment between a query binder subsequence and reference binder subsequence, and/or a sequence alignment between a query target subsequence and reference target subsequence. Preferably the similarity operation uses the BLOSUM80 matrix.

In certain embodiments the similarity operation may comprise: generating a bipartite graph comprising a first set of nodes and a second set of nodes, the first set of nodes containing only binder subsequences and the second set of nodes containing only target subsequences, edge weights of the bipartite graph being equal to the associated known binding values; and determining a monopartite projection of the bipartite graph for the first set of nodes and/or the second set of nodes, wherein the similarity scores are edge weights of the monopartite projection.

In these embodiments a similarity score for a pair of nodes of the first set may be computed by determining a set of common nodes of the second set to which both nodes of the pair of nodes of the first set are connected; and computing a linear correlation between the corresponding edge weights of the bipartite graph. A similarity score for a pair of nodes of the second set may be computed by determining a set of common nodes of the first set to which both nodes of the pair of nodes of the second set are connected; and computing a linear correlation between the corresponding edge weights of the bipartite graph.

The positions of contact amino acid residues may be determined according to a contact point map.

The step of determining contact positions may further comprise simulating a virtual query binder subsequence for use in the contact point map based on the query binder subsequence, wherein the virtual query binder subsequence has a different length to the query binder subsequence, and/or simulating a set of contact points for use in the contact point map. An amount of contact points in the set of contact points may be different from a length of the query binder subsequence and/or reference binder subsequence. In this way the method may be applicable to different lengths, for example where k<9, or k>9, for a 9-mer contact point map. Preferably the contact point map may be defined to contain different length information. In certain embodiments, the method may comprise reducing, or expanding, a larger, or smaller, query binder subsequence to fit the contact point map or mapping multiple amino acid residues to a contact point so that the physical effect of the contact point map results in a set number of pockets.

In certain embodiments the maximum length of a query binder subsequence may be L, L>1, and the set of one or more query binder subsequences may comprise all possible subsequences of the first amino acid sequence of length between 1 and L.

The similarity operation may comprise weighting each reference binder-target subsequence pair according to the amino acid positions of the respective reference binder subsequence.

Preferably the second amino acid sequence may be an MHC protein sequence. More preferably the MHC protein sequence may be an HLA protein sequence.

Computing the binding affinity may comprise computing a product of a reference data matrix, a query data transpose matrix, and a vector of the reference binding values, wherein entries of the reference data matrix are indicative of presence or absence of reference subsequences in respective reference binder sequences and/or reference target sequences, and entries of the query data transpose matrix are indicative of presence or absence of reference subsequences in respective query binder sequences and/or query target sequences; and wherein the entries of the reference data matrix and the entries of the query data matrix are weighted according to the similarity scores. In this embodiment the product may be computed via a sparse matrix computation technique.

The present invention is applicable to both MHC class I molecules and MHC class II molecules.

According to a further aspect of the invention there may be provided a method of generating at least one candidate protein-binding peptide, the method comprising: obtaining amino acid sequences of a plurality of peptides and an amino acid sequence of a protein; determining, for each peptide, a predicted binding affinity to the protein, by a method according to any one of the above aspects of the invention; and selecting one or more candidate peptides of the plurality of peptides based on the respective predicted binding affinity.

The amino acid sequence of the protein may be obtained by one of: serological antibody testing, oligonucleotide hybridisation methods, nucleic acid amplification based methods (including but not limited to polymerase chain reaction based methods), automated prediction based on DNA or RNA sequencing, de novo peptide sequencing, Edman sequencing or mass spectrometry.

The method may further comprise synthesising the one or more candidate peptides.

Additionally, the method may further comprise encoding the candidate peptide into a corresponding DNA or RNA sequence. Further the method may comprise incorporating the sequence into a genome of a bacterial or viral delivery system to create a vaccine.

Thus, peptide, DNA or RNA based vaccines are more reliably constructed for an individual patient as binding affinity can be more effectively predicted, particularly where little or no reference data is available for alleles. The invention has demonstrated competitive performance to that of tools of the art in a cross-validation evaluation and superior performance for any subset of alleles that have little or no coverage in available reference data.

According to a further aspect of the invention there may be provided a binding affinity prediction system for predicting a binding affinity of a query binder molecule to a query target molecule, the query binder molecule having a first amino acid sequence and the query target molecule having a second amino acid sequence, the system comprising at least one processor in communication with at least one memory device, the at least one memory device having stored thereon instructions for causing the at least one processor to perform a method according to any one of the above aspects of the invention.

BRIEF DESCRIPTION OF THE DRAWINGS

Embodiments will now be described in detail, by way of example only, with reference to the accompanying figures, in which:

FIGS. 1A and 1B show an embodiment of a method for predicting binding affinity of a binder to a target;

Figure 3:
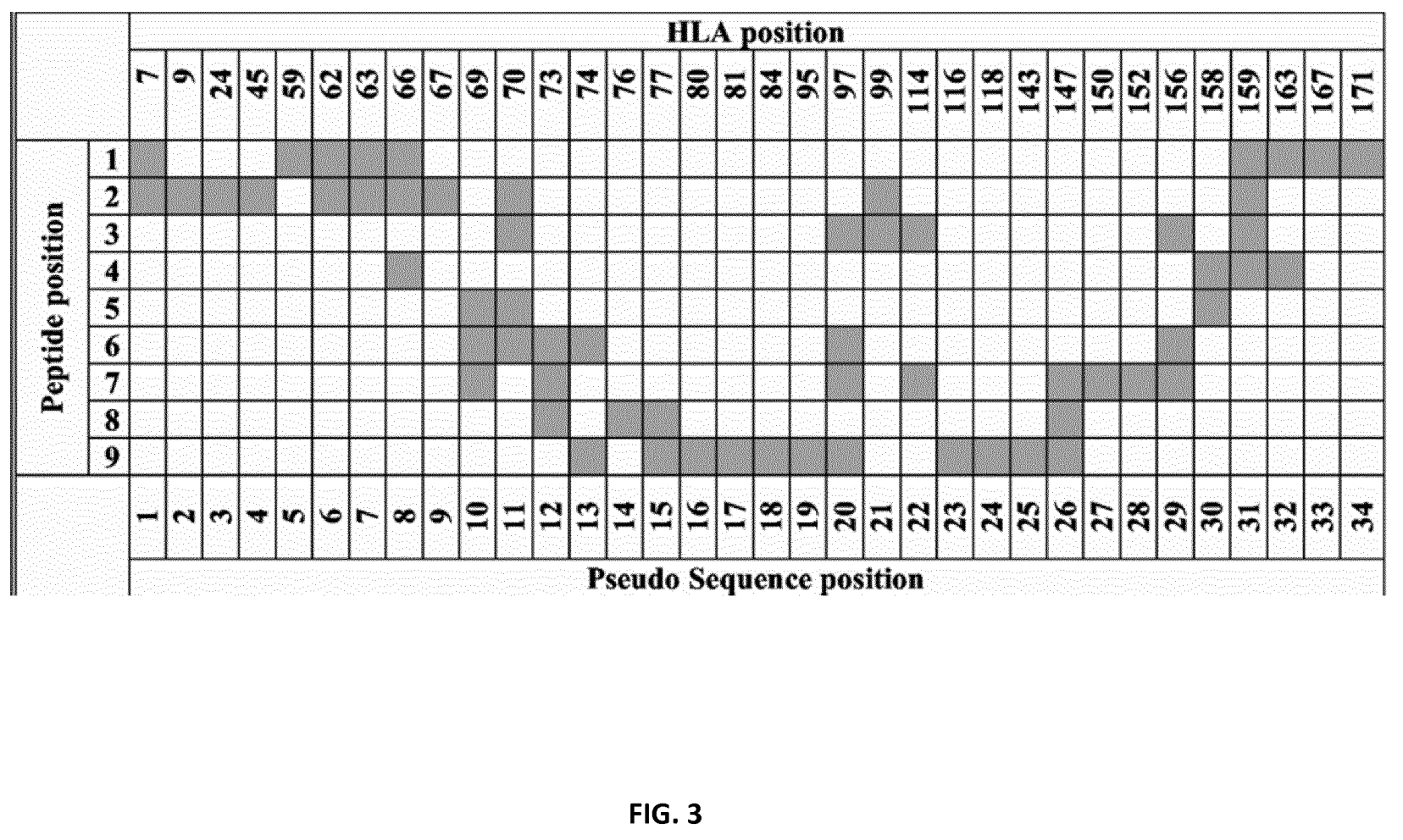

FIG. 3 shows an example of a contact map for use in the method of FIGS. 1A and 1B;

FIG. 4 shows examples of target (MHC) subsequences generated for use in the method;

FIG. 5 to FIG. 7 depict stages in generation of reference data for use in the method;

DETAILED DESCRIPTION

Figure 2:
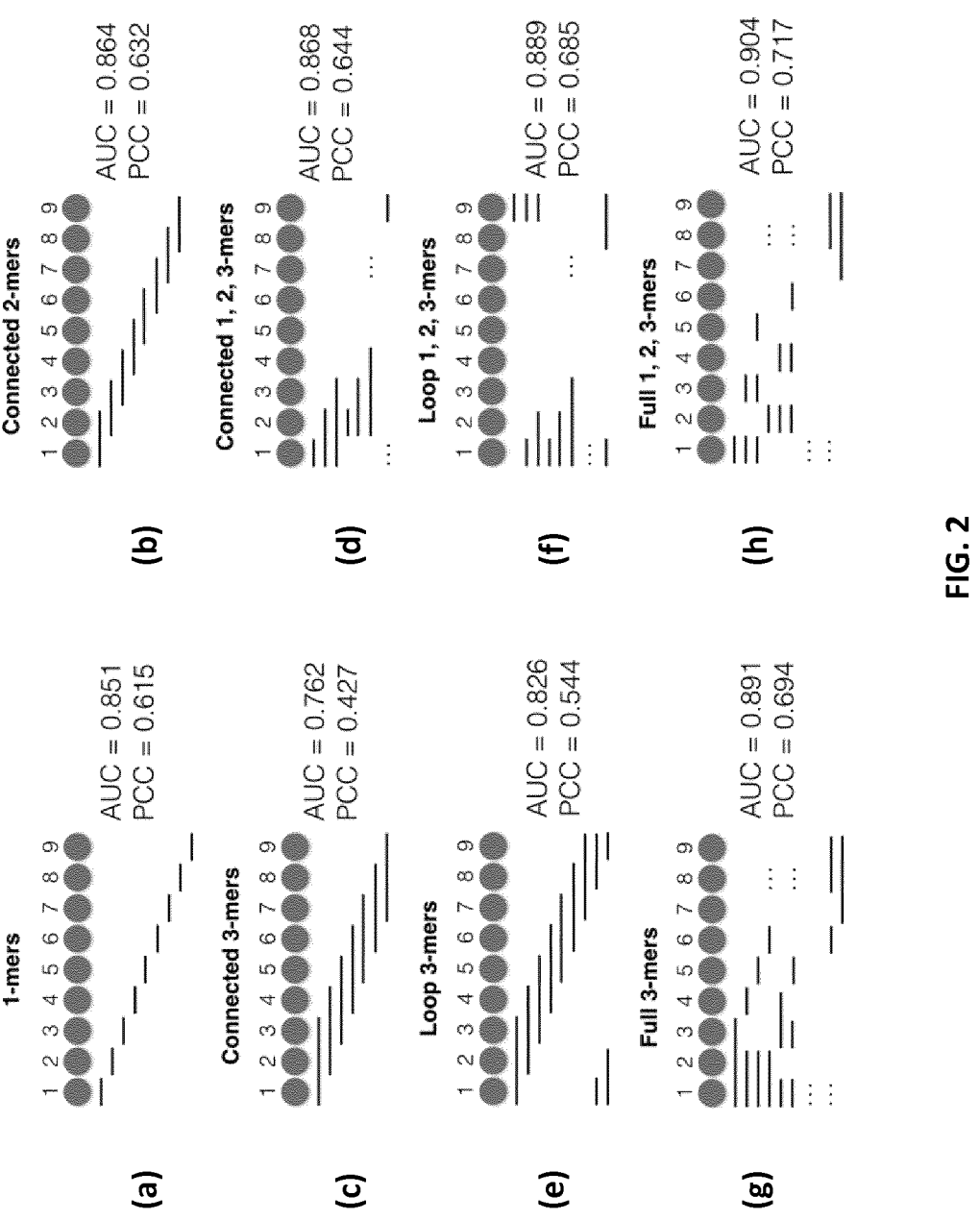
FIG. 2 schematically depicts generating a representation of an amino acid sequence as a set of subsequences.

Methods according to certain embodiments enable computational predictions of a binding affinity of a query binder molecule, such as a peptide, to a query target molecule, such as a protein. The query binder molecule and query target molecule each have a respective amino acid sequence. The predictions are made on the basis of reference data comprising reference binder-target pairs, each pair having a known (measured) binding value, which may be an $IC_{50}$ value measured in nM, or other value based on $IC_{50}$, for example. The reference data may also be referred to herein as training data.

The binding value need not be a direct measure of binding affinity so long as it reflects the relative binding strength between a binder and a target (i.e., relative to other binder-target pairs). Typically, the reference data may be at least partly obtained from a public database such as the Immune Epitope Database (IEDB), GPCRdb or BRENDA.

Referring to FIG. 1, a method 100 according to certain embodiments comprises a step 105 of accessing the reference data store of reference binder-target pairs. Each reference binder-target pair comprises a reference binder amino acid sequence, such as a peptide sequence, and a reference target amino acid sequence, such as an MHC protein sequence. The following discussion will focus on peptide-MHC binding, but it will be understood that the methods and systems discussed below may be readily adapted to other data sets where paired binder sequences and target sequences and corresponding binding values are available.

In order to generate a prediction for a query peptide-MHC pair which is not in the reference data, a method according to embodiments first generates (step 110) a representation of the query peptide sequence as a set of one or more query peptide subsequences which collectively span across the query peptide sequence, at least one of these subsequences being two or more amino acids in length. For example, one possible representation is generated by decomposing the peptide sequence into all possible contiguous 2-mers, as shown in FIG. 2(b), in which the 2-mers are tiled across, and therefore collectively span, the peptide sequence in over-lapping fashion at 1-residue intervals. Another possible representation is in terms of 3-mers, in which at least some of the 3-mer subsequences are not contiguous, as shown in FIG. 2(g). Again, the entire length of the 9-mer peptide is collectively spanned by the 3-mers (i.e., each peptide residue is contained in at least one of the 3-mers).

Next, for each query peptide subsequence, the method determines (step 115) contact positions of contact amino acid residues in the query MHC sequence. Typically, this is done by using an appropriate contact map. For example, for MHC class I sequences, the contact map of Nielsen et al, which is reproduced in FIG. 3, may be used. In general, however, any contact point map, predicted or experimental, could be used. Using the Nielsen et al contact map, the first 2-mer of FIG. 2(b), which has positions (1, 2), would have corresponding contact positions c=(7, 9, 24, 45, 59, 62, 63, 66, 67, 70, 99, 159, 163, 167, 171) in the query MHC sequence.

Analogously to the binding pocket terminology of the prior art, the non-monomeric binding units of the present embodiments may be described as "higher-order pockets", or HOPs. In the context of peptide-MHC binding, the individual query peptide subsequences may be referred to as query peptide HOPs, and the corresponding query MHC subsequences, which are assembled from the MHC residues at the corresponding contact positions (e.g. as derived from a contact map), may be referred to as query MHC HOPs. Each HOP is therefore a subsequence of either the peptide or the MHC sequence, as appropriate. The process of generat-ing a HOP from a peptide or MHC sequence, using one or more sets of amino acid positions of the sequence, may be referred to as a HOP decomposition.

Once a query MHC HOP has been determined for each query peptide HOP, the HOP pairs may be stored (e.g., in RAM or in a database) as query peptide-MHC subsequence (HOP) pairs.

Next, the method generates (step 120), using the reference binder-target (peptide-MHC) pairs, a reference data set. The reference data set may comprise a plurality of rows, each row containing a reference peptide subsequence, a reference MHC subsequence, and a reference binding value. The reference peptide subsequences are reference peptide HOPs which are generated using the same amino acid positions as those used to generate the query peptide HOPs. Similarly, the reference MHC subsequences are MHC reference HOPs which are generated using the same contact positions as used to generate the query MHC HOPs. A reference peptide-MHC HOP pair is associated with a reference binding value which is equal to the binding value of the peptide-MHC pair from which the HOPs were derived.

A particular example of HOP decomposition and the generation of a reference data set will now be described with reference to FIG. 4 to FIG. 7. The sequences shown are not real MHC or peptide sequences, but are simply chosen for illustration purposes. As shown in FIG. 5, binding values are available for alleles HLA-X and HLA-Y bound to one of a number of different peptides, but in the present example, it is desired to predict binding, to allele HLA-X, of a new peptide ABYDEFGHI which is not represented in the reference data, and of a peptide ABCDEFGHI which is repre-sented in the reference data but for which binding to allele HLA-Z is unknown. The HOP decomposition is illustrated only for positions (1, 2) and (1, 3) of the peptide but it will be understood that the same procedure is used for other positions of the peptide as needed to collectively span the entire peptide sequence in the manner discussed above.

The full sequences of the three alleles are not shown, but for the three positions (1, 2, 3), the corresponding MHC HOPs can be generated by using an appropriate contact map as described above. In the example illustrated in FIG. 4, each peptide residue is in proximity with 3 MHC residues accord-ing to the particular contact map used. It will be understood that, in general, different peptide residues may be in prox-imity with fewer or more MHC residues than this, depending on the exact form of the contact map or other means used to determine the contact positions.

For query peptide ABYDEFGHI, the peptide HOP at positions (1, 2) is generated by determining the amino acids at those positions along the sequence, i.e. AB. Similarly, the peptide HOP at positions (1, 3) is AY. The corresponding MHC HOPs for the two sets of positions for allele HLA-X are given by the concatenation of the HOPs shown in FIG. 4. Thus, for positions (1, 2), the MHC HOP for HLA-X is ABCDEF, and for positions (1, 3), the MHC HOP is ABCABD.

The same process may be carried out for the reference data, as shown in FIG. 5. For example, as shown in the first row, peptide ABCDEFGHI has a HOP decomposition AB at positions (1, 2), and a HOP decomposition AC at positions (1, 3). The MHC HOPs for HLA-X need not be regenerated, since the reference MHC sequence in this case is the same as the query MHC sequence.

As shown in FIG. 5, each peptide HOP-MHC HOP pair has an associated binding value which is equal to the binding value of the peptide-MHC pair from which it was generated. Because HOP decompositions for different sequence pairs are not necessarily unique, the method may include a further step of computing a summary of the different binding values for repeated HOP pairs, for example by taking the mean or the median of the binding values. This is illustrated in FIG. 5, where, for example, the binding value of the pairing ABCDEF-AB is computed as the mean of the individual values (0.9, 0.8, 0.8, 0.9, 0.5).

Once all the HOP decompositions have been performed for the reference peptide and MHC sequences, and an appropriate summary computed for repeated HOP pairs, the result is a reference data set comprising, in this case, two tables: a first table 510 for contact position (1, 2), and a second table 520 for contact position (1, 3). It will be appreciated that, in the case of a full set of contact positions which spans across the entire peptide sequence, further tables of reference data will be generated in order to create the reference data set.

Returning to FIG. 1B, in the next step 125 of the method, at least one sequence similarity operation is performed on the respective query peptide-MHC HOP pairs and the ref-erence peptide-MHC HOP pairs to generate a plurality of similarity scores for each query peptide-MHC HOP pair.

In one example, the similarity score may be given a value of 1 in the case of an exact match between the query HOP pair and the reference HOP pair, and a value of 0 otherwise. Thus, for example, query HOP pair AB-ABCDEF at position (1, 2) of the peptide would be assigned a similarity score of 1, since it matches exactly with AB-ABCDEF in the first row of the reference data table in FIG. 5, but AY-ABCABD at position (1, 3) would be assigned a score of 0 because there is no match in the reference data table in FIG. 5.

In another example, the similarity score may be computed using an amino acid substitution matrix, such as the one shown in FIG. 4. This enables the inclusion of contributions to the binding affinity prediction from sequences that are similar (in a biologically meaningful way), but not identical, to the query sequence. The similarity score may be computed separately for the peptide HOPs and MHC HOPs. Thus, for example, an exact match may be enforced for the peptide HOP, but a substitution matrix may be used for the MHC HOP.

For example, the query MHC allele HLA-Z is not represented in the reference data of FIG. 5, but has been determined to have MHC HOP ABCDEX at position (1, 2), and ABCXYD at position (1, 3). Although ABCDEX does not have any exact matches in the reference data for position (1, 2), if the substitution matrix in FIG. 4 is used, a (normalised) similarity score of 0.79 can be computed, and used to weight the contribution of ABCDEX to the overall binding affinity prediction as will be explained in more detail below.

In another example, the similarity score may be computed using a network neighbourhood similarity operation, in which a bipartite network is generated from the MHC HOPs and peptide HOPs, with the edge weights of the network being the binding values of the respective peptide-MHC pairs, and monopartite projections of the network performed, as will be explained in further detail below.

Returning to FIG. 1B, the next step 130 of the method includes computing the binding affinity for the query peptide to the query MHC protein as a weighted combination, typically a sum, of the binding values (from the reference data) of the reference peptide-MHC HOP pairs. The weights of the weighted combination are based on the similarity scores, and may include contributions from more than one similarity operation. For example, both sequence similarity and network neighbourhood similarity may be applied.

Embodiments extend the concept of binding pockets beyond the monomer approach and perform inference based on all possible n-mer pockets within a k-mer peptide-MHC complex, for $k \geq n \geq 1$, to improve MHC-peptide binding prediction. By encompassing higher-order MHC-peptide pockets, the influence of contextual amino acid n-mer length residues in both the peptide and MHC molecule is included, thereby improving the accuracy of the binding affinity prediction in a way which better represents the biological complexity of MHC-peptide binding.

By incorporating sequence and neighbourhood similarity alone, or jointly, it is possible to make predictions for MHC alleles which are not well represented (or are not represented at all) in the available reference data. The present method provides an improved physically interpretable, highly generalizable MHC-peptide binding predictor.

Further aspects of the above embodiments will now be described in more detail.

HOP Decomposition

In one example, the binding of a k-mer peptide to an MHC binding cleft, for example a 9-mer, can be modelled as eight 2-mer MHC-peptide binding-pocket interactions, seven 3-mer binding-pocket interactions, and so forth as (k−n+1) number of n-mer interactions. We will denote this approach, using only contiguous n-mer segments, as the "connected" approach. FIGS. 2(*b*) and 2(*c*) illustrate the connected approach for 2-mer and 3-mer peptide HOPs.

In another example, the linear peptide can be considered as a closed loop. For 3-mer HOPs generated from a 9-mer peptide, this entails adding the "loop-connected" 3-mers consisting of the peptide positions (8, 9, 1) and (9, 1, 2). While such embodiments lose some aspects of physical interpretability by modelling the MHC-peptide interaction in this way, they are advantageous in that they rectify a possible bias towards the central peptide residues in the connected approach. In the case of 3-mers, for instance, the terminal peptide amino-acid positions 1 and 9 in the connected approach will only be covered by one 3-mer each, (1, 2, 3) and (7, 8, 9) respectively. Residue position 2 and 8 will be covered by two 3-mers, and the remaining positions by three 3-mers. Using the closed-loop decomposition approach, there will always be nine n-mers decomposed from a 9-mer. We call this the "loop" approach. The loop approach is illustrated for 3-mers in FIG. 2(*e*).

In a further example, we can consider all possible n-combinations for the MHC-peptide binding pocket interaction in question, where the number of n-mers is given by the binomial coefficient $$\binom{k}{n},$$

where k is the length or the full peptide. For 2-mers and 3-mers, for instance, there are $$\binom{9}{2} = 36, \text{ and } \binom{9}{3} = 84$$

possible n-mer combinations respectively. While straying even further from physical interpretability, since most n-mers are now non-contiguous, this decomposition approach greatly increases the chance of finding MHC-peptide binding pocket interactions that match between the query and the reference data. Additionally, there is no position bias. We call this the "full" approach. This is illustrated for 3-mers in FIG. 2(*g*).

For a peptide of length k=9 bound to an MHC molecule, whose 9 binding pockets are given by a contact point map, we define the following for a n-mer MHC-peptide binding pocket interaction:

A contact position consists of k non-repeated numbers (from 1 to 9 for a nonamer), indicating the positions of the peptide residues, and corresponding MHC binding pockets (e.g., derived according to a contact map).

A Higher-Order Pocket (HOP) is the realisation of the MHC-peptide binding complex, i.e. the k bound peptide residues and the corresponding MHC binding pockets, at the given contact position.

A peptide HOP is the peptide component of a HOP. For example, the contact position (1, 3, 4), and peptide "ABCDEFGHI", result in the peptide HOP "ACD".

An MHC HOP is the MHC component of a HOP, as discussed above in the context of FIG. 1.

Embodiments of the present method can be applied by using a single n-value and a single approach ("full", "loop" or "connected"), or by combining several n-values and approaches. The "full" approach has been found to give superior performance in general.

For the purposes of the discussion below, the following HOP function H may be defined:

$$H : (c, I, X) \rightarrow (i, x)_c, \tag{1}$$

where I is an MHC molecule, X a peptide, and $c \in C(n)$ a single contact position among the set of contact positions C for the approach and n-value in question. $(i, x)_c$ denotes the HOP realisation of I and X at contact position c, where i is the MHC HOP, and x is the peptide HOP. We denote MHC molecules by I and J, MHC HOPs by the corresponding lowercase letters i and j, full peptides by x and Y, and the peptide HOPs correspondingly by x and y. It should be noted that only HOPs belonging to the same contact position c can be directly compared, and that it is possible for unequal MHC-peptide pairs, (I, X), to decompose into several identical HOPs, $(i, x)_c$, so long as there is a suitable overlap in the MHC and peptide amino acid sequences, as discussed above.

Consider a query MHC-peptide pair (I, X) with unknown binding affinity, and HOP components H(c, I, X)→$(i, x)_c$. Given a reference data set of MHC-peptide pairs (J, Y), with corresponding binding affinities $w_{JY}$, and HOP components H:(c, J, Y)→$(j, y)_c$, the following expression can be used to predict the binding affinity contribution from the single HOP component $(i, x)_c$ to the binding affinity between I and X:

$$\hat{p}_{IX}(c, Sim) = \frac{\sum_{\{(j,y)_c\}} Sim(i, j; x, y) \cdot \hat{w}_{jy}(c, I, X)}{\sum_{\{(j,y)_c\}} |Sim(i, j; x, y)|}, \tag{2}$$

where $\{(j, y)_c\}$ is the set of all unique HOPs with $c \in C(k)$. Furthermore, Sim $(i, j; x, y)$ is a general similarity metric providing a quantitative similarity score between any two HOPs $(i, x)_c$ and $(j, y)_c$. The weights may be represented by the general expression $$\hat{w}_{jy}(c, I, X) = \frac{\sum_{\{H(c,J,Y)=(j,y)_c\}} GlobalSim(I, J; X, Y) \cdot w_{JY}}{\sum_{\{H(c,J,Y)=(j,y)_c\}} |GlobalSim(I, J; X, Y) \cdot w_{JY}|}, \tag{3}$$

where $\{H(c, J, Y)=(j, y)_c\}$ is the set of all entries in the reference data for which the MHC-peptide pair (J, Y) decomposes to HOP (j, y), and $w_{JY}$ is the transformed binding affinity value associated with MHC-peptide pair (J, Y). The similarity operator GlobalSim(I, J; X, Y) is HOP independent, i.e. "global" within the framework, and provides a quantitative similarity score between any two MHC-peptide pairs (I, X) and (J, Y). In certain embodiments, GlobalSim (I, J; X, Y)≡1, which is the equivalent of letting Equation (3) simply be the average over the binding affinity values for all MHC-peptide pairs containing the HOP $(j, y)_c$. Typically, all similarity metrics are defined to be in the range from 0 to 1, where 1 implies perfect similarity while 0 implies no, or minimal, similarity.

Equation (2) expresses the contribution from a single contact position to the total binding affinity prediction of MHC-peptide pair (I, X). By summing over all contact positions for the n-mer approach in question, it is possible to calculate the binding affinity prediction for a query MHC-peptide pair (I, X) by the following:

$$p_{IX}(n, Sim) = \frac{\sum_{c \in C(n)} A(c) \cdot \hat{p}_{IX}(c, Sim)}{\sum_{c \in C(n)} A(c)}, \tag{4}$$

where A(c) is an anchor-value weight allowing certain positions to be given more importance than others in the MHC-peptide binding interaction. Peptide positions 2 and 9 are examples of such positions for HLA binding.

In certain embodiments, it may be desirable to include the possibility of having multiple n-values, with multiple associated similarity metric choices. In such embodiments, therefore, the binding affinity prediction may be obtained by summing over contributions from the different combinations of n and Sim as follows:

$$P_{IX} = \frac{\sum_{\{n,Sim\}} f(n, Sim) \cdot N(n, Sim) \cdot p_{IX}(n, Sim)}{\sum_{\{n,Sim\}} f(n, Sim) \cdot N(n, Sim)}, \tag{5}$$

where N(n, Sim) is the number of unique HOP matches for the n and Sim in question, i.e. the number of nonzero sum elements in Equation (2) across all contact positions c in Equation (4). The remaining quantity, f(n, Sim), is an importance-weight value enabling flexibility when combining several individual approaches, by, for instance, letting 3-mers be given twice the importance as 2-mers. Equation (5) may be considered as a way to ensemble over multiple approaches, allowing several models based on various similarity metrics and n-values to contribute to each binding affinity prediction.

From the above Equations (2, 4, 5), it will be apparent that the present method provides flexibility in that many different choices of the HOP similarity metric Sim (i, j; x, y) are possible.

In certain embodiments, similarity operations on peptide HOPs and MHC HOPs are performed separately. As such, the general similarity metric may be expressed as follows:

$$Sim(i,j;x,y)=MHCSim(i,j) \cdot PepSim(x,y), \tag{6}$$

where MHCSim(i, j) provides the similarity score between MHC HOPs i and j, and PepSim(x, y) the similarity score between peptide HOPs x and y.

Figure 8:
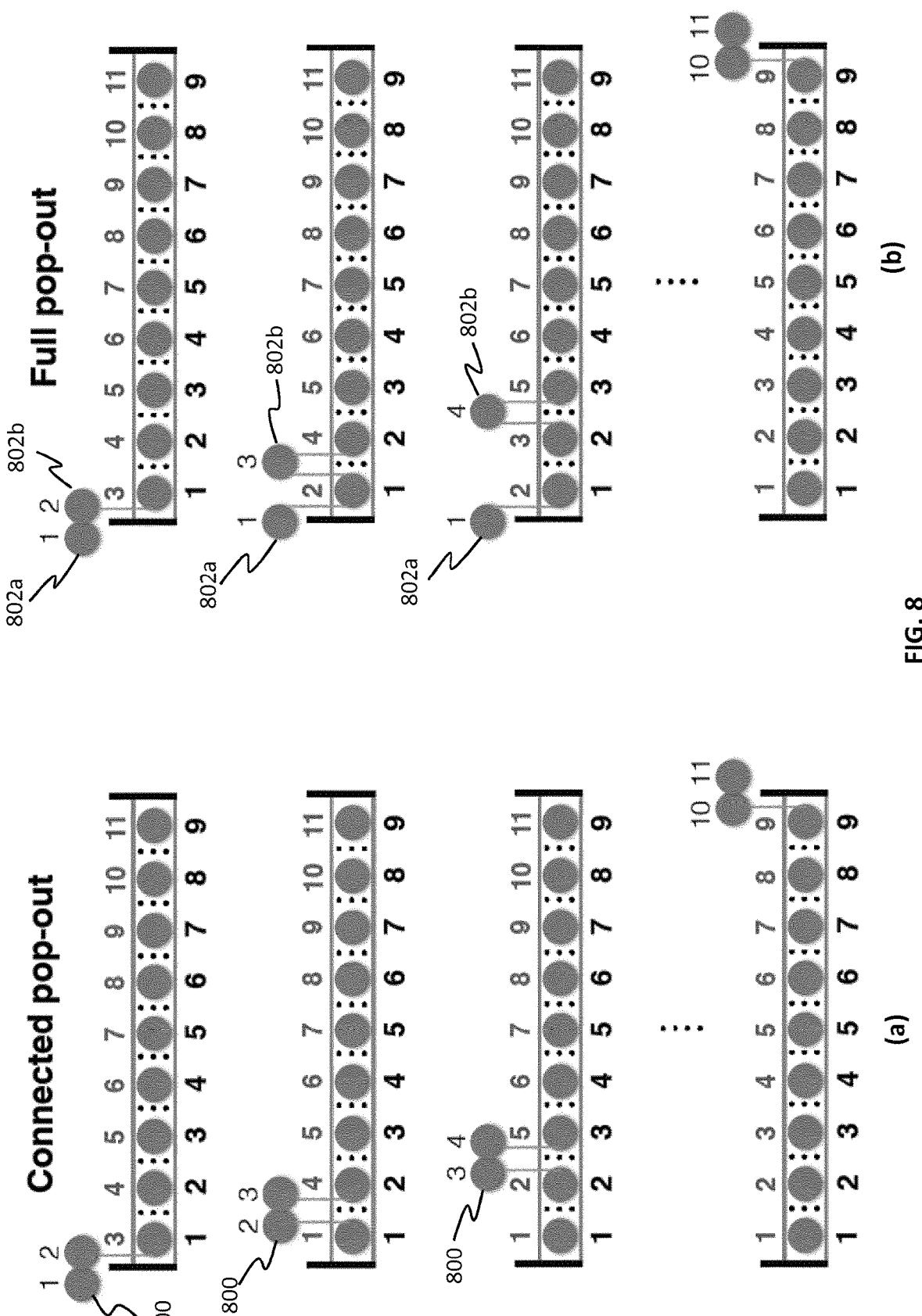
FIG. 8 to FIG. 10 depict various methods of adapting a query amino acid sequence which is mismatched with a reference amino acid sequence.
Figure 9:
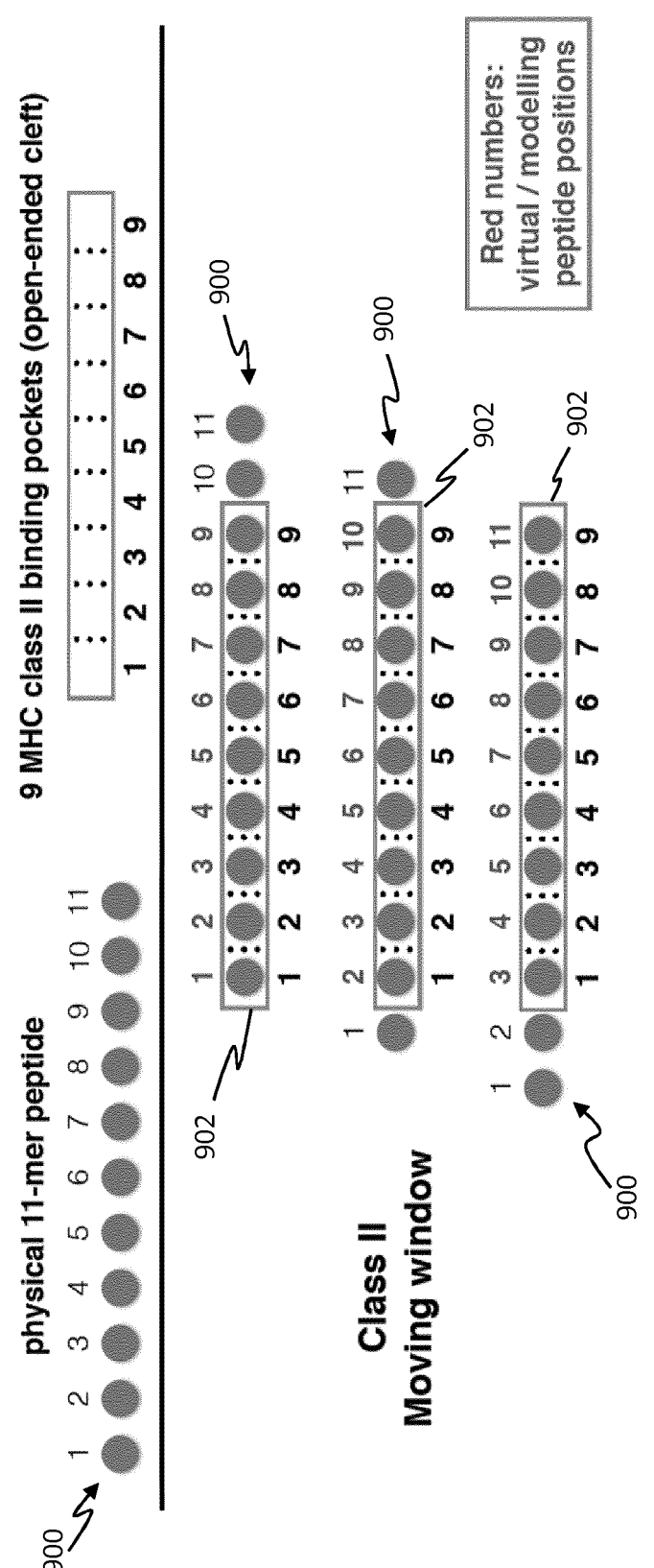
Figure 10:
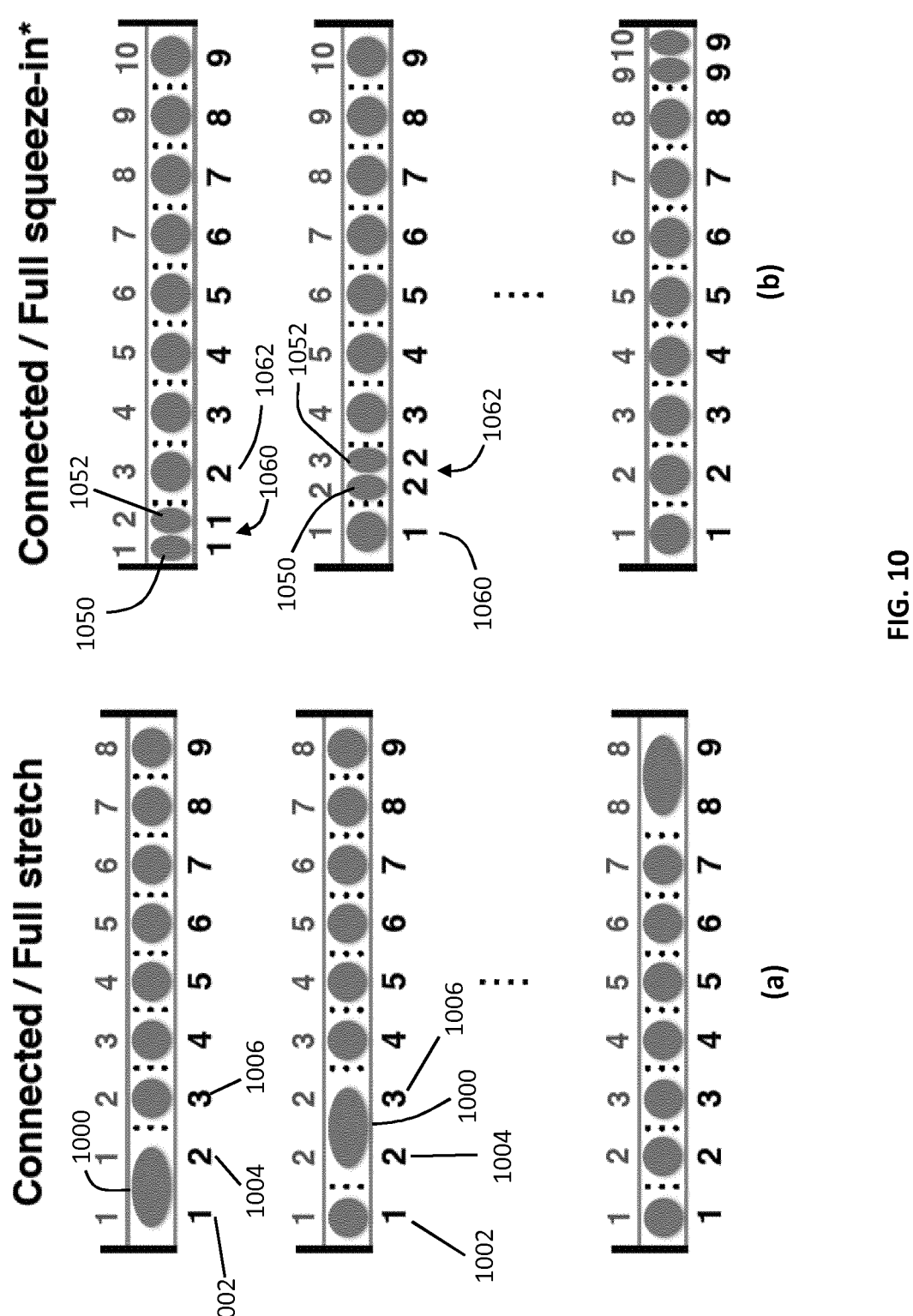

In certain embodiments, the length of a query peptide may be different than the length k of peptides in the reference data and/or the contact point map. In this case, the query peptide may be transformed to one or more "virtual" k-mers. Different ways of doing this are illustrated in FIGS. 8 to 10. Similarly, the set of contact points may be simulated so as to create a "virtual" MHC binding cleft or a "virtual" pocket as will become clear from the following example.

For example, if the reference data contains 9-mers and the query peptide is an 11-mer, in a "connected" approach to the problem, one can pass a bulge 800 of 2 amino acids through the entire peptide, starting and ending with the 2 outermost amino acids hanging off either end of the binding cleft, as shown in FIG. 8(a). There are 10 such virtual peptides per physical 11-mer (not 9, since there are 2 ends and 8 "in-betweens" in a 9-mer peptide). Another approach, termed the "full" approach, illustrated in FIG. 8(b), allows for bulges and hang-offs (802a, 802b) of length 1, and thus results in many more virtual peptides, $$\binom{11}{2} = 55$$

in total. It should be noted that the "full" approach results in a combinatorial explosion of number of virtual peptides for large k, since $$N = \binom{k}{k-9}$$

for k>9. Another approach, called the "moving window" approach, is illustrated in FIG. 9 and results in 3 virtual peptides 902 for each physical 11-mer 900.

The "moving window", "connected" and "full" approaches are applicable to k<9 as well, but with bulges and hang-offs substituted by gap insertions. The number of virtual peptides is also lower, compared to k>9, since the physical peptide is smaller.

For k<9, we can also implement a peptide "stretching" framework, as shown in FIG. 10(*a*), where single amino acids 1000 can occupy more than one pocket, e.g. adjacent pocket pairs (1002, 1004) or (1004, 1006). That is, instead of inserting gaps, duplicates of adjacent amino acids can be inserted to simulate single amino acids being stretched across pockets.

For k>9, we can additionally implement a peptide "squeezing" approach, where one or more peptide positions are duplicated, squeezing two amino acids into the duplicated, single MHC pocket, as shown in FIG. 10(*b*). For example, amino acids 1050 and 1052 can be "squeezed" into pocket 1060, or pocket 1062, and so on.

In some embodiments, the above methods can be combined, for example by allowing all k>9 approaches to be combined, and all k<9 approaches to be combined, using optimisation, or other learning methods, to find which virtual peptide/MHC configurations make the most sense across the data. For example, various combinations of the different methods may be applied to one or more training data sets, and the combination which gives the best performance when applied to a test data set may be selected as the optimal combination. Accordingly, a binding affinity prediction made using the combined approaches may comprise a weighted sum over the binding affinity prediction contributions from every virtual peptide-MHC pair, resulting in one binding affinity prediction per physical peptide-MHC pair.

As will have been noted, "virtual" k-mer or binding cleft can be considered to be a simulation which allows for multiple length queries to be utilised with the contact point map. In conventional contact point maps, a linear fixed length peptide is mapped to a fixed length set of MHC residues. For different lengths, the peptide may be broken into combinations of k-mers and each combination is processed.

In an example of the simulated k-mer technique proposed, a subset of the k-mer query peptide may be mapped to a subset of the contact points. Multiple peptide amino acids can be mapped to any number of pockets and therefore the residue to any pocket by translating (or transcoding) the query k-mer into a different sequence that can be mapped to the contact points.

The examples above include reducing (or expanding) a larger (or smaller) query peptide to fit a contact point map or mapping multiple amino acids to a contact point so that the physical effect results in a set number of pockets.

In this way the contact point map technique may be applicable to different peptide lengths, for example where k<9, or k>9, for a 9-mer contact point map. The contact point map may be defined to contain different length information. In effect, the technique can be applied to k-mers of different lengths than those the contact point map is "designed" for. There is proposed a way to address complex interactions between two three-dimensional proteins/molecules so long as there is a way to express the contact points between target amino-acid subsequences and binder amino-acid subsequences (even for many-to-many non-contiguous amino-acid subsequences).

Examples of Similarity Metrics Sim (i, j; x, y)

Basic Similarity

In one form, the components of the similarity metric Sim(i,j;x,y) in Equation (6) may be expressed as:

$$MHCSim(i, j) = \begin{cases} 1, & i = j \\ 0, & i \neq j \end{cases}, \quad PepSim(x, y) = \begin{cases} 1, & x = y \\ 0, & x \neq y \end{cases}. \tag{7}$$

This is equivalent to requiring that the query HOP exactly matches at least one entry in the reference data set for it to contribute to the binding affinity prediction. By applying these metrics, Equation (2) can be written as $$\hat{p}_{IX}(c) = \frac{\sum_{\{(j=i, y=x)_c\}} \hat{w}_{jy}(c, I, X)}{N}, \tag{8}$$

where N is the number of exact HOP matches found in the reference data.

Sequence Similarity

In some embodiments, a similarity operation may comprise determining a sequence similarity between a query peptide HOP and a reference peptide HOP, and/or a sequence similarity between a query MHC HOP and a reference MHC HOP.

The individual MHC similarity factor in Equation (6) can be written as:

$$MHCSeqSim(i, j) = \frac{SeqSim(i, j)^\alpha}{SeqSim(i, i)^\alpha}, \tag{9}$$

and equivalently for the peptide sequence similarity, PepSeqSim(x,y). The parameter α is a tuning parameter which, as will be understood, may be applied in order to provide a soft threshold, as it regulates the influence of strong similarities compared to weak ones without removing data explicitly (a hard threshold, on the other hand, would set similarity scores below the threshold to zero). Allowing such a parameter to be tuned during training may lead to far better model performance than if α=1. Model performance may be assessed using the Pearson correlation coefficient between the true and predicted binding values, and the area under an receiver-operator characteristic (ROC) curve (AUC) which is generated by treating data points with IC50 values≤500 nM as being in the bound class and those with values above that threshold as being in the non-bound class. These metrics will be referred to throughout as PCC and AUC respectively In certain embodiments, the sequence similarity can be determined using BLOSUM alignment. Advantageously, the use of the BLOSUM80 matrix has been found to result in the best performance (again, as measured by PCC and AUC) among the BLOSUM matrices tested by the present inventors. However, it will be appreciated that other scoring matrices, whether based on evolutionary considerations, physico-chemical considerations (such as vector of topological and structural information for coded and noncoded amino acids—VTSA, and/or principal components score Vectors of Hydrophobic, Steric, and Electronic properties—VHSE), or both, may also be used.

Bipartite Network Neighbourhood Similarity

In some embodiments, a similarity operation may comprise determining a network neighbourhood similarity. In such embodiments, for a given contact position c, a bipartite network (graph) can be generated, in which the MHC and peptide HOP components i and x are the top and bottom nodes, respectively. There are no direct connections, or edges (links), between any two MHC HOPs or any two peptide HOPs. All direct edges are between MHC HOPs and peptide HOPs, with binding affinity values as associated edge weights. Using the covariance of these edge weights across the top or bottom nodes (MHC or peptide HOPs) in the bipartite network, it is possible to make predictions for HOPs that do not exist in the reference data. In the case of the MHC HOP neighbourhood similarities, for instance, the weighted monopartite projection of the MHC-peptide HOP network is determined by replacing all peptide HOPs shared by any pair of MHC HOPs with a single weight value indicating how similarly the MHC HOP pair interacted with the set of shared peptide HOPs. There are multiple ways to determine the weight value, but it has been found that the linear correlation between pairs of binding affinities provides the best performance in terms of PCC and AUC. The MHC HOP factor in Equation (genSim) can then be expressed as $$MHCNbrSim(i, j) =$$

$$\left( \frac{1}{2} + \frac{N\sum_{y} w_{iy}w_{jy} - \sum_{y} w_{iy}\sum_{y} w_{jy}}{2\sqrt{N\sum_{y} w_{iy}^2 - \left(\sum_{y} w_{iy}\right)^2}\sqrt{N\sum_{y} w_{jy}^2 - \left(\sum_{y} w_{jy}\right)^2}} \right)^{\alpha}, \quad (10)$$

where N is the number of shared neighbour peptide HOPs (bottom nodes) y between MHC HOPs (top nodes) i and j, and the w's are effective binding affinity weight values for the subscripted MHC HOP pair in question (in the generalized framework, Equation (3) can be applied to these weight values as well). An equivalent expression is used for the peptide neighbourhood similarity, PepNbrSim(x,y).

Although the neighbourhood similarity operation cannot enable inference for de novo HOP components, it is advantageous in that the test data is not needed to calculate the similarity scores. In other words, the model can be trained without any prior knowledge of the test data. This can allow for shorter prediction times, which may be preferred over short training times in at least some circumstances. It also simplifies the implementation of other techniques, such as bootstrapping.

In some embodiments, alternatives to Equation (10) are possible. For monopartite networks, the weighted topological overlap (wTO) metric has previously been applied successfully to various biological systems. See, for example, K. Nowick, T. Gernat, E. Almaas, and L. Stubbs, "Differences in human and chimpanzee gene expression patterns define an evolving network of transcription factors in brain," Proceedings of the National Academy of Sciences, vol. 106, no. 52, pp. 22358-22363, 2009, the entire contents of which are incorporated herein by reference.

The wTO between node/vertex i and j can be calculated by:

$$wTO_{ij} = \frac{\sum_{n}^{N} a_{in}a_{nj} + a_{ij}}{\min(|k_i|, |k_j|) + 1 - |a_{ij}|}, \quad (10a)$$

where $a_{ij}$ is an element in the weighted adjacency matrix of the network and $k_i$ is the weighted/unweighted connectivity (node strength/degree) of node i. Accordingly, a bipartite version of this metric may be used as the HOP neighbourhood similarity metric, i.e. can replace the right-hand side of Equation (10). It can be expressed as:

$$bwTO_{ij} = \frac{\sum_{k}^{N} a_{ix}a_{xj}}{\min(|k_i|, |k_j|)}, \quad (10b)$$

Where bwTO stands for "bipartite weighted topological difference", i, j are top nodes and x are bottom nodes and ka is the bipartite equivalent to the connectivity in the wTO expression (sum over bottom node neighbours). If the denominator is zero, the bwTO value is also zero. A similar "bipartite weighted topological difference" (bwTD) metric may alternatively be used in place of Equation (10b):

$$bwTD_{ij} = \frac{\sum_{k}^{N} |a_{ix} - a_{xj}|}{\sum_{k}^{N} \max(|a_{ix}| - |a_{xj}|)}. \quad (10c)$$

Both bwTO and bwTD have been found to perform well in some contexts, but Equation (10) has emerged as the overall best neighbourhood similarity choice based on prediction performance (PCC and AUC).

Similarity Parameters

For both sequence and neighbourhood similarity, and other conceivable similarity approaches, it may be advantageous to apply a tuning parameter $\alpha$, as done in Equations (9) and (10), in order to adjust the similarity scores in such a way that similar HOPs are given the appropriate binding affinity contribution when compared to dissimilar HOPs. In embodiments where the similarity values range between 1 (identical) and 0 (dissimilar), we can apply a to adjust the ratios between similarity values whilst preserving their ordering. It may also be advantageous to apply a similarity cut-off, either in the form of a minimal similarity score, or in the form of a fixed maximal number m of similar scores. In the case of MHC sequence similarity, for instance, where MHCSim=MHCSeqSim and PepSim is the Basic, binary similarity metric, Equation (2) can be written as $$\hat{p}_{ix}(c, MHCSeqSim) = \frac{\sum_{j}^{m} \sum_{y} SeqSim(i, j)^{\alpha} \cdot w_{jy}}{\sum_{j}^{m} \sum_{y} |SeqSim(i, j)^{\alpha}|}, \quad (11)$$

where the sum over j to m simply means that we sum over the m MHC HOPs j that are most similar to MHC HOP i.

Parameter Optimisation

There are several free parameters in the general framework, ranging from the similarity-metric specific parameters, such as tuning parameters and cut-off values, to the more generally applicable parameters, such as anchor-position weights and approach-importance weights, f (n, Sim). Various optimisation strategies can be used for finding these parameters, including both local and global methods.

In some embodiments, the stepwise parameter optimisation approach detailed below may be used. It will be appreciated, though, that many other parameter optimisation processes may be performed using various methods known to those skilled in the art.

1. The anchor weights, A(c), have been found to be broadly unaffected by changes to the experimental setup, so long as they are evaluated in a pan-allele setup. They are thus the first parameter class we find. Several optimisation schemes would be suitable, but we chose to apply differential evolution (DE) since it is possible to optimise for best AUC values, which together with the global nature of DE, is thought to provide parameters less prone to overfitting. Full basic HOP pairs for 1, 2, and 3-mers can be chosen as predictor for this step. The DE algorithm is run several times for several train/test folds to ensure generalised parameters, and the average anchor values are passed on to the next step. It should be noted that only the 9 monomer anchor weights are considered variables, since the remaining higher-order anchor weights are calculated as averages over their monomer contributions.

2. This step is specific to each similarity approach, defined by an n value (number of pockets in the approach) and a similarity metric, i.e. the (n, Sim) in the equations. Here, full basic HOP pairs for 1, 2, 3-mers with the anchor parameters found in the previous step is combined with the specific (neighbourhood or sequence) similarity defined by (n, Sim) as the predictor for the optimisation. Using a similar DE optimisation algorithm as in step 1, there are only 2 variables to optimise over for each specific optimisation, namely the sum cut-off parameter m and the power parameter α. DE suits this step nicely, as opposed to local methods (like least squares), since m is an integer. Also here, the optimisation is run several times for several train/test folds to ensure generalised parameters, and the average m and a values (for each specific (n, Sim) approach) are passed on to the next step.

3. Following steps 1 and 2, the anchor weights A (c), and all m and a values needed for the various similarity approaches, have been generated. The remaining part is to tune the prediction contribution parameters f from each (n, Sim) approach so that the overall summed prediction performance is optimal. Curve-fitting parameters (a and b in y=ax+b) may also be added to the optimisation variables in order to get IC50 predictions resembling the actual IC50 measurements in the training data. Since the variable space is smooth and quite well-behaved, least squares optimisation can be used, minimising the overall square distance between the true and predicted values. This is almost equivalent to optimising for large PCC values, which is a desired trait for a regression method. Again, the optimisation is run several times, with different initial conditions, for several train/test folds to generate a list of parameter sets (each found to be optimal for their train/test set and initial conditions). The final parameter set is found by applying some statistical method to this list, through averages (mean, median), largest overall correlation or other methods. By largest overall correlation, we mean the parameter set that has the largest mean correlation to all the other parameter sets, which could thus be called "consensus parameters".

In one example, data from the IEDB may be divided into two subsets, with a first subset used for training, and a second subset used for testing. For example, the first and second subsets may be (1) all binding affinity data added to the IEDB until 2009 (referred to herein as Kim09), and (2) all binding affinity data added between 2010 and 2013 (referred to herein as Kim13). The binding affinity measurements (IC50/EC50) may be transformed using the log-transform: $1-\log(\text{IC50})/\log(500^2)$, where the logarithm base reflects the default threshold value for which an MHC-peptide pair are said to bind (binder has IC50≤500 nM). In addition, part of the data may be omitted in order to assist testing for overfitting, in a procedure referred to as data blinding, for example by reproducibly pseudorandomly omitting 0.5% of the binding data described above.

Evaluation of the method was performed via several numerical experiments: (1) Training on the Kim09 data and testing on the Kim13 data, (2) performing 5-fold cross validation using the predefined 5 folds in the Kim09 data (where a "fold" as used herein refers to a subset of the data that does not overlap with any other subset), (3) training on all data not included in the 0.5% blinded data set and testing on the blind set, and (4) combining the Kim09 and Kim13 data sets, leaving one allele out for testing, while training on all the remaining alleles. The four experiment types are referred to below as: (1) Kim09-Kim13, (2) Kim09 5-fold, (3) Blind, and (4) LOAO (leave-one-allele-out). Two evaluation metrics were used for each experiment: the Pearson's correlation coefficient (PCC) between the true and predicted binding values, and the area under the receiver-operator characteristic (ROC) curve (AUC), using the standard of IC50≤500 nM as the threshold for binding (i.e., a binder and target are classified as bound if the IC50 is less than or equal to the threshold, and unbound otherwise). The ROC curve may be generated by any method known in the art. For example, functions available in the Python packages NumPy and SciPy may be used to generate the ROC curve.

The pan-allele anchor-position weights were found to be highly stable across random subsets, and were chosen to be fixed as the optimal solution for the Kim09 5-fold cross-validation for simplicity. Allele-specific anchors were implemented for the sequence-similarity allele-specific prediction framework, but were not attempted in a pan-allele framework. The similarity-metric specific parameters were found using differential evolution in a 20-fold pseudorandom training scheme where 5 alleles and 5% of the data were left out of the training and used for testing. A more traditional 5-fold cross validation was also tried, resulting in well-performing models for all but the LOAO experiments, which is sensible since these models were then never "forced" to predict for unknown MHC alleles during training. The similarity parameters were also found to be stable for various subsets, after sufficient number of iterations, and were thus also kept static for all pan approaches in the results discussed below. In order to determine approach-importance weights, we opted for a dual training framework where: (1) the models for the LOAO experiments were trained using the same 20-fold cross-validation scheme as above, while (2) the models for the other experiments were trained using standard cross validation, with 1000 random parameter initialisations for each fold, where the final consensus parameters were chosen as the set with the highest average correlation to all the other thousands of parameter sets.

Computation of the Binding Affinity Prediction

In one implementation, the binding affinity predictions in Equations (2), (4) and (5) may be determined by performing appropriate HOP decompositions on the reference data, storing the results in one or more dictionaries or hash tables, and then, for each query HOP, performing a lookup of the stored results. The weighted sums can be computed by looping over different HOP decompositions, similarity metrics, and so on.

Alternatively, some implementations may use a sparse matrix encoding in order to compute the binding affinity. For example, SciPy's sparse matrix library can be used along-side NumPy functionality to achieve both memory effectiveness and speed far outmatching a more straight-forward iterative dictionary implementation.

We start by defining the matrix H, which is an (#data rows×#HOP IDs) matrix. The HOP IDs are integers uniquely identifying any MHC-peptide (binder-target) HOP. For every data row, there is an MHC sequence (pseudosequence) and a peptide, which can be decomposed into N HOPs (N=9 if only monomer HOPs are included). For data row p, every HOP has an associated HOP ID q. Starting with the Basic framework, all these (p, q) pairs are given a value of 1.0 in the matrix. For reference, the sum of each row in this Basic matrix is N.

The matrix comes in two flavours, "train" and "test", where $H_{train}$ is constructed using the training (reference) data, while $H_{test}$ is constructed using the test (query) data. In its most simple form (no anchors, no duplicate HOP averaging), Basic predictions can then be found by $$P = [H_{test} \times H_{train}^T \times y] \oslash [H_{test} \times H_{train}^T \times \mathbb{1}], \quad (12)$$

where y is a column vector of shape (#train data rows×1) containing the binding affinity values associated with the training data, $\mathbb{1}$ is a unit vector with the same shape as y, and P is a prediction vector of shape (#test data rows×1) containing the predictions. The $\oslash$ operator denotes element-wise division, so the rightmost brackets can be considered to contain the normalisation.

To average over duplicate HOPs, we perform a sum along the columns of $H_{train}$, leaving us with a row vector of shape (1×#HOP IDs). Expanding this sum vector along the columns to the shape of $H_{train}$, we can perform an element-wise division operation with the sum matrix, denoted by M:

$$H_{train} = H_{train} \oslash M. \quad (13)$$

Similarly, if we want to apply anchor weights, we simply perform an element-wise multiplication (notation: $\odot$) between the anchor-weights matrix A, which has the same shape as H, and either $H_{test}$ or $H_{train}$. For reference, A has a maximum of N unique values, and all columns consist of equal elements (since it is the same HOP). Implementation-wise, this is not as cumbersome as it seems, because we can exploit this predictable structure of A avoiding making a dense H-shaped matrix. The same is true for the above operation with M. Applying anchors:

$$H = H \odot A. \quad (14)$$

Thus far, we have not considered similarities. Adding similarities to the framework generally affects the entire process, including anchor-weights and normalisations, and must be applied before any other operation. If using neighbourhood similarity or sequence similarity or both, there is no longer N HOPs for each row. Rather, the number of HOPs per row is affected by n, Sim, m and α and is, in general, unequal for each row. A common feature for all rows, however, is that there are always just N elements per row equal to 1.0 (for non-zero α). The other elements are given a similarity value $\in [0, 1)$. The process of populating the matrix with these similarity elements may be as follows:

1. For each HOP (decomposed from data row p), find the m most similar HOPs existing in the data.
2. For each HOP, find the HOP IDs q matching the m hits found in 1.

3. Let element (p, q) be equal to the similarity score between the origin HOP and the similar HOP as given by Sim and a.

In the above, HOP can be an MHC-peptide (full) HOP, MHC HOP, or peptide HOP, depending on the chosen approach. This can be done for multiple similarities, so that $$H = H_{Basic} + H_{simA} + H_{SimB} + \dots, \quad (15)$$

so long as there are no overlapping elements between the similarities (if so, some rule must be applied to ensure that elements are between 0 and 1).

Typically, sequence similarities are only applied to the "test" matrix, since the query sequences determine which similarities we need to calculate for the predictions. Neighbourhood similarities would typically only be applied to the "train" matrix, since NbrSim is limited to making predictions for MHC and peptide HOPs already existing in the training data.

Sequence and neighbourhood similarities may be incorporated into the prediction as follows (self-similarities are removed from NbrSim and SeqSim, since they are already contained in the Basic matrix):

$$H_{train} = H_{train\ Basic} + H_{train\ NbrSim}. \quad (16)$$

M is found from $H_{train}$ in similar fashion to the sum matrix M discussed above. Then, $$H_{train} = H_{train} \oslash M.$$

Furthermore, adding anchors:

$$H_{train} = H_{train} \odot A.$$

The query matrix is $$H_{test} = H_{test\ Basic} + H_{test\ SeqSim},$$

and the predictions are found, as before, by $$P = [H_{test} \times H_{train}^T \times y] \oslash [H_{test} \times H_{train}^T \times \mathbb{1}].$$

If, as mentioned above, the query peptide is a different length k than the reference peptides, then predicting the binding affinity for a single k-mer may be done using these steps:

The k-mer is transformed into virtual peptide-MHC pairs using one, or a combination, of the decomposition methods described earlier.

A binding affinity value is predicted for each virtual peptide-MHC pair (called "virtual prediction" below).

The binding affinity of the k-mer is found by one of:

Selecting the value of the best (lowest IC50 value) virtual prediction.

Calculating the average (mean, median, etc.) of all virtual predictions.

Averaging over a subset of virtual predictions, such as the top 10%, or top 3, best values.

Performing a weighted average of all virtual predictions, if a set of virtual peptide-MHC pair importance weights can be acquired.

Evaluation Results

Basic Pan-Allele Method

The Basic pan-allele method (Equations (7) and (8)) was applied, using the HOP decomposition depicted schematically and labelled "Full 1, 2, 3-mers" in FIG. 2(h). We also allowed for optimisation over anchor and approach weight values, A (c) and f (n) in Equations (4) and (5) respectively. Using the validation experiments outlined above, we obtained the performance shown in Table 1 for the 1, 2, and 3-mer Basic pan-allele method. Each of the Tables here are for 9-mers to demonstrate the techniques described. The method provided an AUC-value of 0.920 and PCC-value of 0.752 for the Kim09-Kim13 experiment, with comparable values for the Kim09 5-fold cross validation. These values surpass the reported values for methodologically comparable tools, such as PickPocket, Nebula and sNebula. Advantageously, therefore, the basic pan-allele version of the present method is able to achieve predictions competitive with allele specific approaches, but without requiring large amounts of training data.

The LOAO predictions had an overall weighted-average of AUC=0.849 and PCC=0.608. In some cases, predictions for alleles that share very few (HLA-A-01-01 and HLA-A-29-02), or no (HLA-B-46-01), MHC HOPs with the MHC alleles in the training set, were worse than average.

Pan-Allele Method with Sequence Similarity Inference

Adding sequence similarity inference by making use of Equation (9) effectively increases the size of the training data, where data points stemming from MHC-peptide pairs with sufficiently similar sequences to the query HOP are also added. The sequence similarity approach can be applied with respect to MHC HOPs, peptide HOPs or both at the same time, as outlined above. To generate the results below, we considered only the single-factor similarity metrics, i.e. MHC and peptide sequence similarity, and not the higher-order sequence similarity metric combining both of the aforementioned similarity factors.

The sequence similarity method performance slightly surpassed the Basic method performance overall, with AUC=0.926 and PCC=0.765 for the Kim09-Kim13 experiment, for instance. As shown in Table 2, the results of the LOAO experiments show considerable improvement for alleles such as HLA-A-01-01, HLA-A-29-02 and HLA-B-46-01, which have few or no exact MHC HOP matches in the training data. Advantageously, by allowing the method to draw upon data from MHC alleles/peptides with similar sequence segments to the query allele/peptide, we see a great increase in the performance for these alleles. The AUC increases from 0.551 to 0.795 for HLA-A-01-01, from 0.5 (i.e. random) to 0.930 for HLA-B-46-01, with corresponding increases for the PCC values. The total weighted average of the sequence similarity LOAO performance results in an AUC-0.900, and a PCC=0.683, which is respectable considering that all predictions were made for alleles not contained in its predictor's training data. These results indicate that the sequence similarity method can generalise well for de novo, or underrepresented alleles in the training data.

Pan-Allele Method with Neighbourhood Similarity Data Imputation

The neighbourhood similarity method is, like the sequence similarity method, an extension to the Basic method, wherein contributions from MHC and peptide HOPs sharing binding characteristics across the reference data are included, as described above.

The pan-allele network neighbourhood similarity method adds MHC and peptide HOP neighbourhood similarities to the Basic pan-allele 1, 2, and 3-mer method, analogous to the sequence similarity approach. The performance of the neighbourhood similarity method is shown in Table 3. A moderate increase in both AUC and PCC scores over the Basic method was observed. The scores are nearly identical to those of the sequence similarity method. The Kim09-Kim13 test yields AUC=0.928, and PCC=0.766. These across-allele experiments showcase the strength of the neighbourhood approach in the situation where the query HOP components are generally well-covered in the training data.

The LOAO experiments followed the overall trend of the Basic method results (Table 1), with an average AUC=0.850 and PCC=0.616, albeit with significant variations for some individual alleles.

Pan-Allele Method with Combined Similarity Strategies

Combining the sequence similarity and neighbourhood similarity approaches allows the present method to incorporate the advantages of both sequence and network neighbourhood similarity strategies, by leveraging the combination of training data imputation with sequence similarity inference. For the combined strategy, we permitted n-mer HOPs of lengths greater than 3, which, mostly, resulted in slight performance increases if the test data closely resembled the training data, with significant decreases otherwise, due to overfitting tendencies. The LOAO experiment was therefore restricted to 1-, 2-, and 3-mers, as before. The combined LOAO results closely resemble those of the sequence similarity approach, although with slight, to substantial, improvements for almost all alleles, resulting in an average AUC=0.921 and PCC=0.731.

As shown in Table 4, the combined approach improves upon the previous approaches for all experiments, with AUC=0.930 and PCC=0.770 for the Kim09-Kim13 test, as shown in FIG. 5, and similar increases for the other experiments. The models were not altered or tweaked after the unblinding of the Blind data set, which clearly hints at good generalisability whilst also providing superior performance over the other approaches.

It will be appreciated from the above discussion that embodiments of the present method provide improved performance compared to the monomer centric pocket-based approaches of the prior art in predicting MHC-peptide binding affinity for alleles that have little or no coverage in the training databases. At least some limitations of prior art methods can be overcome through the integration of similarity inferences from n-mer HOP bipartite network neighbourhoods and/or sequence alignments. The performance of the integrated general framework and network inference exceeds that of the methodologically comparable pan-allele approaches, reaching an overall performance approaching the best-in-class neural network approaches for the standard IEDB data performance tests. The average AUC scores of 0.93 to 0.95, and PCC scores of 0.77 to 0.81, demonstrate both superior classification and regression capabilities of the described approach. The most convincing results that demonstrate the powerful utility of embodiments of the present method can be seen in the LOAO experiments, demonstrating an average performance of AUC=0.92 and PCC=0.73. The present method is therefore capable of making useful binding affinity predictions for uncommon, little studied MHC alleles.

In this document we provide a clear use of the method in design of vaccines. However it will be understood that the techniques described herein could equally apply to designing tailored T-cells that recognise the identified targets. Similarly the techniques could also be used to identify neoantigen burden in a tumor and where this is used as a biomarker, i.e. predicting response to therapy.

Figure 11:
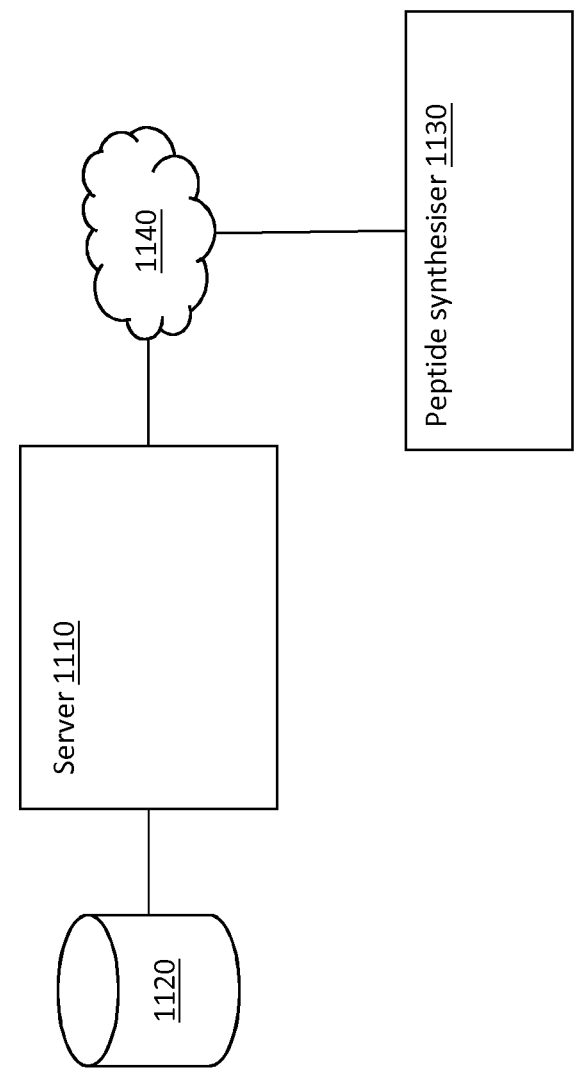
FIG. 11 shows an example of a system suitable for implementing the method.

Turning now to FIG. 11, an example of a system suitable for implementing embodiments of the method is shown. The system 1100 comprises at least one server 1110 which is in communication with a reference data store 1120. The server may also be in communication with an automated peptide synthesis device 1130, for example over a communications network 1140.

In certain embodiments the server may obtain amino acid sequences of a plurality of peptides and an amino acid sequence of a protein and determine, for each peptide, a predicted binding affinity to the protein using the steps described above. Based on the respective predicted binding affinity the server may select one or more candidate peptides of the plurality of peptides.

The candidate peptides may be sent to the automated peptide synthesis device 1130 to synthesise the peptide. The automated peptide synthesis device 1130 generates target epitopes synthetically, i.e in this example target peptides. Techniques for automated peptide synthesis are well known in the art and it will be understood that any known technique may be used. Typically, the target peptide is synthesized using standard solid phase synthetic peptide chemistry and purified using reverse-phase high performance liquid chromatography before being formulated into an aqueous solution. If used for vaccination, prior to administration the peptide solution is usually admixed with an adjuvant before being administered to the patient Peptide synthesis technology has existed for more than 20 years but has undergone rapid improvements in recent years. For brevity we do not describe in detail such machines but their operation would be understood to one skilled in the art and such conventional machines may be adapted to receive a candidate protein from the server.

The server may comprise the functions described above to predict binding affinity of a query binder molecule to a query target molecule. The respective binding affinities may be sent to a further processing module to identify a target epitope based on the binding affinity suitable for the creation of a vaccine. However, the server may also be operable to identify a target epitope for vaccine design. It will of course be understood that these functions may be subdivided across different processing entities of a computer network and different processing modules in communication with one another. For example, the server may receive one or more query molecules over a computer network and return a suitable binding affinity or set of candidate epitopes. The query may be received electronically from a computer network or inputted to a graphical user interface.

The techniques for predicting binding affinity and, based on that binding affinity, for identifying a candidate peptide may integrate into a wider ecosystem for customised vaccine development. Example vaccine development ecosystems are well known in the art and are described at a high-level for context but for brevity we do not describe the ecosystem in detail.

In an example ecosystem, a first, sample, step may be to isolate DNA from a tumor biopsy and matched healthy tissue control. In a second, sequence, step, the data is sequenced and the variants identified i.e. the mutations. In an immune profiler step the associated mutated peptides may be generated «in silico».

Using the associated mutated peptides, and the techniques described here, a neoantigen may be predicted and selected and target epitopes identified for vaccine design. That is, the candidate peptide sequence chosen based on its predicted binding affinity determined using the technique described herein.

The target epitopes are then generated synthetically using conventional techniques as described above. Prior to administration the peptide solution is usually admixed with an adjuvant before being administered to the patient (vaccination).

The suitable target epitopes predicted by the methods described herein may also be used to create other types of vaccine other than peptide based vaccines. For example the peptide targets could be encoded into the corresponding DNA or RNA sequence and used to vaccinate the patient. Note that the DNA is usually inserted in to a plasmid construct. Alternatively the DNA can be incorporated into the genome of a bacterial or viral delivery system (can be RNA also—depending on the viral delivery system)—which can be used to vaccinate the patient-so the manufactured vaccine in a genetically engineered virus or bacteria which manufactures the targets post immunisation in the patient i.e. in vivo.

Figure 12:
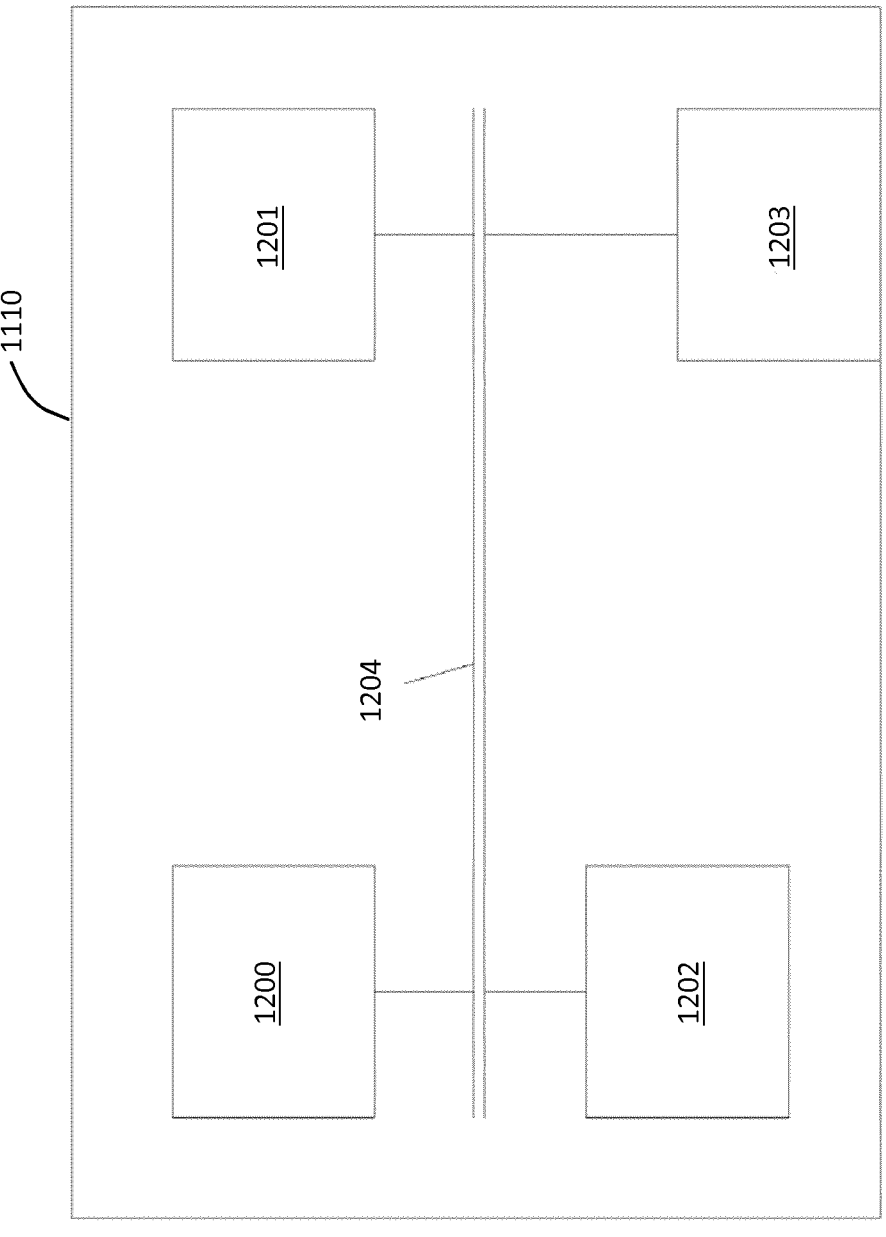
FIG. 12 shows an example of a server.

An example of a suitable server 1110 is shown in FIG. 12. In this example, the server includes at least one microprocessor 1200, a memory 1201, an optional input/output device 1202, such as a keyboard and/or display, and an external interface 1203, interconnected via a bus 1204 as shown. In this example the external interface 1203 can be utilised for connecting the server 1110 to peripheral devices, such as the communications networks 1140, reference data store 1120, other storage devices, or the like. Although a single external interface 1203 is shown, this is for the purpose of example only, and in practice multiple interfaces using various methods (e.g. Ethernet, serial, USB, wireless or the like) may be provided.

In use, the microprocessor 1200 executes instructions in the form of applications software stored in the memory 1201 to allow the required processes to be performed, including communicating with the reference data store 1120 in order to receive and process input data, and/or with a client device to receive sequence data for query binder molecules and query target molecules, and to generate binding affinity predictions according to the methods described above. The applications software may include one or more software modules, and may be executed in a suitable execution environment, such as an operating system environment, or the like.

Accordingly, it will be appreciated that the server 1200 may be formed from any suitable processing system, such as a suitably programmed client device, PC, web server, network server, or the like. In one particular example, the server 1200 is a standard processing system such as an Intel Architecture based processing system, which executes software applications stored on non-volatile (e.g., hard disk) storage, although this is not essential. However, it will also be understood that the processing system could be any electronic processing device such as a microprocessor, microchip processor, logic gate configuration, firmware optionally associated with implementing logic such as an FPGA (Field Programmable Gate Array), or any other electronic device, system or arrangement. Accordingly, whilst the term server is used, this is for the purpose of example only and is not intended to be limiting.

Whilst the server 1200 is a shown as a single entity, it will be appreciated that the server 1200 can be distributed over a number of geographically separate locations, for example by using processing systems and/or databases 1201 that are provided as part of a cloud based environment. Thus, the above described arrangement is not essential and other suitable configurations could be used.

TABLE 1

| | | Basic method results | | |
|---|---|---|---|---|
| | With censored data | | Without censored data | |
| | AUC | PCC | AUC | PCC |
| Kim09-Kim13 | 0.920 | 0.752 | 0.808 | 0.598 |
| Kim09 5-fold | 0.932 | 0.774 | 0.846 | 0.684 |
| Blind data | 0.939 | 0.788 | 0.863 | 0.673 |
| LOAO: | | | | |
| HLA-A-01-01 | 0.551 | 0.071 | 0.539 | 0.086 |
| HLA-A-03-01 | 0.872 | 0.629 | 0.751 | 0.484 |
| HLA-A-11-01 | 0.885 | 0.704 | 0.778 | 0.580 |
| HLA-A-26-01 | 0.910 | 0.679 | 0.806 | 0.629 |
| HLA-A-29-02 | 0.548 | 0.104 | 0.515 | 0.040 |
| HLA-B-46-01 | 0.500 | 0.000 | 0.500 | 0.000 |
| HLA-B-54-01 | 0.679 | 0.295 | 0.648 | 0.250 |
| HLA-B-57-01 | 0.885 | 0.661 | 0.766 | 0.557 |
| HLA-B-58-01 | 0.911 | 0.669 | 0.858 | 0.648 |
| Total average | 0.849 | 0.608 | 0.749 | 0.486 |

TABLE 2

| | | Sequence similarity method results | | |
|---|---|---|---|---|
| | With censored data | | Without censored data | |
| | AUC | PCC | AUC | PCC |
| Kim09-Kim13 | 0.926 | 0.765 | 0.818 | 0.619 |
| Kim09 5-fold | 0.939 | 0.790 | 0.855 | 0.703 |
| Blind data | 0.946 | 0.801 | 0.872 | 0.693 |
| LOAO: | | | | |
| HLA-A-01-01 | 0.795 | 0.429 | 0.703 | 0.401 |
| HLA-A-03-01 | 0.903 | 0.697 | 0.784 | 0.559 |
| HLA-A-11-01 | 0.941 | 0.779 | 0.878 | 0.717 |
| HLA-A-26-01 | 0.932 | 0.716 | 0.810 | 0.648 |
| HLA-A-29-02 | 0.850 | 0.619 | 0.797 | 0.596 |
| HLA-B-46-01 | 0.930 | 0.502 | 0.635 | 0.368 |
| HLA-B-54-01 | 0.874 | 0.676 | 0.815 | 0.601 |
| HLA-B-57-01 | 0.956 | 0.803 | 0.849 | 0.729 |
| HLA-B-58-01 | 0.946 | 0.768 | 0.905 | 0.757 |
| Total average | 0.900 | 0.683 | 0.783 | 0.562 |

TABLE 3

| | | Neighbourhood similarity method results | | |
|---|---|---|---|---|
| | With censored data | | Without censored data | |
| | AUC | PCC | AUC | PCC |
| Kim09-Kim13 | 0.928 | 0.766 | 0.820 | 0.620 |
| Kim09 5-fold | 0.938 | 0.789 | 0.855 | 0.702 |
| Blind data | 0.946 | 0.804 | 0.869 | 0.694 |
| LOAO: | | | | |
| HLA-A-01-01 | 0.540 | 0.072 | 0.530 | 0.068 |
| HLA-A-03-01 | 0.875 | 0.650 | 0.753 | 0.499 |
| HLA-A-11-01 | 0.872 | 0.679 | 0.754 | 0.541 |
| HLA-A-26-01 | 0.918 | 0.676 | 0.774 | 0.585 |
| HLA-A-29-02 | 0.547 | 0.087 | 0.529 | 0.051 |
| HLA-B-46-01 | 0.500 | 0.000 | 0.500 | 0.000 |
| HLA-B-54-01 | 0.734 | 0.390 | 0.686 | 0.309 |
| HLA-B-57-01 | 0.906 | 0.713 | 0.771 | 0.574 |
| HLA-B-58-01 | 0.949 | 0.765 | 0.886 | 0.716 |
| Total average | 0.850 | 0.616 | 0.747 | 0.486 |

TABLE 4

| | | Combined method results | | |
|---|---|---|---|---|
| | With censored data | | Without censored data | |
| | AUC | PCC | AUC | PCC |
| Kim09-Kim13 | 0.930 | 0.770 | 0.823 | 0.627 |
| Kim09 5-fold | 0.942 | 0.801 | 0.860 | 0.713 |
| Blind data | 0.947 | 0.814 | 0.873 | 0.709 |
| LOAO: | | | | |
| HLA-A-01-01 | 0.831 | 0.472 | 0.736 | 0.444 |
| HLA-A-03-01 | 0.911 | 0.710 | 0.802 | 0.590 |
| HLA-A-11-01 | 0.945 | 0.793 | 0.883 | 0.731 |
| HLA-A-26-01 | 0.940 | 0.725 | 0.831 | 0.671 |
| HLA-A-29-02 | 0.858 | 0.635 | 0.802 | 0.613 |
| HLA-B-46-01 | 0.934 | 0.527 | 0.634 | 0.375 |
| HLA-B-54-01 | 0.889 | 0.703 | 0.836 | 0.639 |
| HLA-B-57-01 | 0.956 | 0.805 | 0.849 | 0.729 |
| HLA-B-58-01 | 0.960 | 0.800 | 0.907 | 0.759 |
| Total average | 0.921 | 0.731 | 0.807 | 0.607 |

The invention claimed is:

1. A computer-implemented method of predicting a binding affinity of a query binder peptide to a query target major histocompatibility complex (MHC) molecule from a subject with cancer, the method comprising:

obtaining, with at least one processor, a first amino acid sequence corresponding to the query binder peptide and a second amino acid sequence with defined residue numbering corresponding to the query target MHC molecule, wherein the first amino acid sequence is encoded by a DNA sequence of a tumor biopsy from the subject;

accessing, with the at least one processor for the subject with cancer, a reference data store of reference binder-target pairs comprising respective paired reference binder amino acid sequences and corresponding reference target amino acid sequences, each reference binder-target pair having an associated known binding value;

generating, with the at least one processor, a representation of the first amino acid sequence as a set of query binder subsequences which collectively span across the first amino acid sequence, each query binder subsequence comprising one or more amino acid residues at respective positions along the first amino acid sequence and having a length less than the length of the first amino acid sequence, wherein at least one of the query binder subsequences comprises two or more amino acid residues;

for each query binder subsequence of the set of query binder subsequences, determining contact positions of contact amino acid residues in the second amino acid sequence from a contact point map comprising the residue numbering and assembling a corresponding query target subsequence from the contact amino acid residues at the contact positions in the contact point map, to thereby generate query binder-target subsequence pairs, such that each query target subsequence represents MHC amino acid residues in proximity to each amino acid residue of the corresponding query binder subsequence according to the contact point map;

generating, with the at least one processor, from the reference binder-target pairs, a reference data set comprising a plurality of sets of reference binder-target subsequence pairs, each reference binder-target subsequence pair in each set of reference binder-target subsequence pairs having a corresponding query binder subsequence in the set of query binder subsequences, each reference binder-target subsequence pair comprising: a reference binder subsequence comprising amino acid residues of the respective reference binder amino acid sequence at positions corresponding to those positions of the corresponding query binder subsequence, and a reference target subsequence comprising amino acid residues of the respective reference target sequence at the contact positions derived from the contact point map;

assigning each reference binder-target subsequence pair a reference binding value based on the known binding value of the reference binder-target pair from which it was generated, such that each reference binder-target pair is decomposed into a set of subsequences corresponding to each of the query binder subsequences and the corresponding query target subsequence, with each set of subsequences assigned the known binding value of the reference binder-target pair;

performing, with the at least one processor, at least one similarity operation on the respective query binder-target subsequence pairs and the sets of reference binder-target subsequence pairs to generate a plurality of similarity scores for each query binder-target subsequence pair, such that the similarity scores for each query binder-target subsequence pair represent a contribution to binding affinity from subsequences in a set of reference binder-target subsequence pairs that are similar to the respective query binder-target subsequence, wherein the at least one similarity operation generates similarity scores by generating a similarity score for a comparison between a query binder subsequence and reference binder subsequence, wherein the at least one similarity operation comprises: generating a bipartite graph comprising a first set of nodes and a second set of nodes, the first set of nodes containing only binder subsequences and the second set of nodes containing only target subsequences, edge weights of the bipartite graph being equal to associated known binding values; and determining a monopartite projection of the bipartite graph for the first set of nodes and/or the second set of nodes, wherein similarity scores are edge weights of the monopartite projection for the first set of nodes and/or the second set of nodes;

computing, with the at least one processor, the binding affinity for the query binder peptide to the query target MHC molecule as a weighted combination of the reference binding values of the sets of reference binder-target subsequence pairs, wherein weights of the weighted combination are based on the plurality of similarity scores for each query binder-target subsequence pair;

determining, with the at least one processor, that the binding affinity for the query binder peptide to the query target MHC molecule satisfies a binding threshold;

selecting, with the at least one processor, responsive to determining that the binding affinity satisfies the binding threshold, the query binder peptide as a candidate peptide for creating a vaccine;

sending, to an automated peptide synthesis device, a peptide sequence corresponding to the candidate peptide to cause the automated peptide synthesis device to create the vaccine including the candidate peptide; and administering to the subject the vaccine including the candidate peptide.

2. The computer-implemented method according to claim 1, wherein the at least one similarity operation generates similarity scores by generating a second similarity score for a comparison between a query target subsequence and reference target subsequence, and combines the similarity score for the comparison between the query binder subsequence and the reference binder subsequence and the second similarity score.

3. The computer-implemented method according to claim 2, wherein the similarity score for the comparison between the query binder subsequence and the reference binder subsequence is given a non-zero value in the case of an exact match, and a zero value otherwise and/or wherein the second similarity score is given a non-zero value in the case of an exact match, and a zero value otherwise.

4. The computer-implemented method according to claim 1, wherein the at least one similarity operation comprises a sequence alignment between a query binder subsequence and reference binder subsequence, and/or a sequence alignment between a query target subsequence and reference target subsequence.

5. The computer-implemented method according to claim 1, wherein a similarity score for a pair of nodes of the first set is computed by determining a set of common nodes of the second set to which both nodes of the pair of nodes of the first set are connected; and computing a linear correlation between the corresponding edge weights of the bipartite graph.

6. The computer-implemented method according to claim 1, wherein a similarity score for a pair of nodes of the second set is computed by determining a set of common nodes of the first set to which both nodes of the pair of nodes of the second set are connected; and computing a linear correlation between the corresponding edge weights of the bipartite graph.

7. The computer-implemented method according to claim 1, wherein the step of determining contact positions further comprises simulating a virtual query binder subsequence for use in the contact point map based on the query binder subsequence, wherein the virtual query binder subsequence has a different length to the query binder subsequence, and/or simulating a set of contact points for use in the contact point map.

8. The computer-implemented method according to claim 1, wherein a maximum length of a query binder subsequence is L, L>1, and the set of one or more query binder subsequences comprises all possible subsequences of the first amino acid sequence of length between 1 and L.

9. The computer-implemented method according to claim 1, wherein the at least one similarity operation comprises weighting each reference binder-target subsequence pair according to the amino acid positions of the respective reference binder subsequence.

10. The computer-implemented method according to claim 1, wherein the second amino acid sequence is a human leukocyte antigen (HLA) protein sequence.

11. The computer-implemented method according to claim 1, wherein computing the binding affinity comprises computing a product of a reference data matrix, a query data transpose matrix, and a vector of the reference binding values, wherein entries of the reference data matrix are indicative of presence or absence of reference subsequences in respective reference binder sequences and/or reference target sequences, and entries of the query data transpose matrix are indicative of presence or absence of reference subsequences in respective query binder sequences and/or query target sequences; and wherein the entries of the reference data matrix and the entries of the query data matrix are weighted according to the plurality of similarity scores for each query binder-target subsequence pair.

12. The computer-implemented method of claim 1, wherein the obtaining step comprises obtaining a plurality of amino acid sequences corresponding to a plurality of query binder peptides, the first amino acid sequence being one of the plurality of amino acid sequences, wherein the computing step further comprises computing, for each peptide of the plurality of query binder peptides, a respective binding affinity to the query target MHC molecule, and wherein selecting the query binder peptide further comprises selecting one or more candidate peptides from the plurality of query binder peptides based on the respective computed binding affinity.

13. The computer-implemented method of claim 12, further comprising a method of making the vaccine which comprises (i) synthesizing the one or more candidate peptides using the automated peptide synthesis device in accordance with the peptide sequence or (ii) encoding the one or more candidate peptides into a corresponding DNA or RNA sequence and optionally incorporating the DNA or RNA sequence into a genome of a bacterial or viral delivery system.

14. The computer-implemented method of claim 1, wherein the binding binder threshold comprises an $IC_{50}$ value of less than or equal to 500 nM.

* * * * *